(12) United States Patent
Yu et al.

(10) Patent No.: US 7,776,844 B2
(45) Date of Patent: Aug. 17, 2010

(54) N-(PHOSPHONOALKYL)-AMINO ACIDS, DERIVATIVES THEREOF AND COMPOSITIONS AND METHODS OF USE

(76) Inventors: Ruey J. Yu, 655 Stump Rd., Chalfont, PA (US) 18914; Eugene J. Van Scott, 3 Hidden La., Abington, PA (US) 19001

( * ) Notice: Subject to any disclaimer, the term of this patent is extended or adjusted under 35 U.S.C. 154(b) by 0 days.

(21) Appl. No.: 12/428,906

(22) Filed: Apr. 23, 2009

(65) Prior Publication Data

US 2009/0208499 A1 Aug. 20, 2009

Related U.S. Application Data

(62) Division of application No. 12/194,203, filed on Aug. 19, 2008, now Pat. No. 7,572,776, which is a division of application No. 11/621,287, filed on Jan. 9, 2007, now Pat. No. 7,429,575.

(60) Provisional application No. 60/757,614, filed on Jan. 10, 2006.

(51) Int. Cl.
*A61K 31/66* (2006.01)
(52) U.S. Cl. .................... 514/114; 514/399
(58) Field of Classification Search ............. 514/114, 514/399; 548/335.5, 170; 558/170, 156
See application file for complete search history.

(56) References Cited

U.S. PATENT DOCUMENTS

| | | | |
|---|---|---|---|
| 3,288,846 A | 11/1966 | Irani et al. | |
| 3,799,758 A | 3/1974 | Franz | |
| 3,853,530 A | 12/1974 | Franz | |
| 5,259,974 A | 11/1993 | Chen et al. | |
| 5,414,112 A * | 5/1995 | Dragisich | 562/12 |
| 6,229,045 B1 | 5/2001 | Ringer et al. | |
| 7,429,575 B2 | 9/2008 | Yu et al. | |
| 2005/0164916 A1 | 7/2005 | Leadbetter et al. | |

OTHER PUBLICATIONS

Strunin et al., 1989, CAS: 111:233525.*
Shi et al., 2004, CAS: 142: 231739.*
Li et al., 2005, CAS; 143:158351.*
Sandeman et al., 2002, CAS: 137: 274431.*
Spengler et al., 1998, CAS: 129:189654.*
Eke et al., 1996, CAS: 124:211429.*
Stahl et al., 1995, CAS: 124:56310.*
Jezowska-Bojczuk et al., 1994, CAS: 120:281638.*
Strumin et al., 1989, CAS: 111:194894.*
Balthazor et al., 1987, CAS: 106: 50457.*
The Merck Index, "An Encyclopedia of Chemicals, Drugs, and Biologicals," (2001) p. 1768, (2 pgs.), 13th Edition, O'Neil et al. (Ed.), Merck & Co., Inc., Whitehouse Station, N.J.
Wester et al., 1991, CAS: 114:242443.

* cited by examiner

*Primary Examiner*—Rei-tsang Shiao
(74) *Attorney, Agent, or Firm*—Panitch Schwarze Belisario & Nadel LLP

(57) ABSTRACT

The present invention relates to an N-(phosphonoalkyl)-amino acid, a related compound or a derivative thereof, the N-(phosphonoalkyl)-amino acid, related compound or derivative thereof being in a form as a free acid, salt, partial salt, lactone, amide or ester, or in stereoisomeric or non-stereoisomeric form, other than N-(phosphonomethyl)-glycine or N,N-bis(phosphonomethyl)-glycine. Also included is a composition including an N-(phosphonoalkyl)-amino acid, a related compound or a derivative thereof in a form as a free acid, salt, partial salt, lactone, amide or ester, or in stereoisomeric or non-stereoisomeric form, and a cosmetically or pharmaceutically acceptable vehicle for topical or systemic administration to a mammalian subject, as well as a method of administering an effective amount of such a composition for alleviating or improving a condition, disorder, symptom or syndrome associated with at least one of a nervous, vascular, musculoskeletal or cutaneous system.

17 Claims, No Drawings

N-(PHOSPHONOALKYL)-AMINO ACIDS, DERIVATIVES THEREOF AND COMPOSITIONS AND METHODS OF USE

CROSS-REFERENCE TO RELATED APPLICATIONS

This application is a divisional application of U.S. patent application Ser. No. 12/194,203, filed Aug. 19, 2008, now allowed, which is a divisional application of U.S. patent application Ser. No. 11/621,287, filed Jan. 9, 2007, now U.S. Pat. No. 7,429,575, issued Sep. 30, 2008, which claims the benefit under 35 U.S.C.§119(e) of U.S. Provisional Application No. 60/757,614, filed Jan. 10, 2006. The entire disclosures of all of the above applications are hereby incorporated herein by reference.

BACKGROUND OF THE INVENTION

The present invention relates to an N-(phosphonoalkyl)-amino acid, a related compound or a derivative thereof, the N-(phosphonoalkyl)-amino acid, related compound or derivative thereof being in a form as a free acid, salt, partial salt, lactone, amide or ester, or in stereoisomeric or non-stereoisomeric form, other than N-(phosphonomethyl)-glycine or N,N-bis(phosphonomethyl)-glycine. The present invention also relates to a composition including an N-(phosphonoalkyl)-amino acid, a related compound or a derivative thereof in a form as a free acid, salt, partial salt, lactone, amide or ester, or in stereoisomeric or non-stereoisomeric form, and a cosmetically or pharmaceutically acceptable vehicle for topical or systemic administration to a mammalian subject, as well as a method of administering an effective amount of such a composition for alleviating or improving a condition, disorder, symptom or syndrome associated with at least one of a nervous, vascular, musculoskeletal or cutaneous system.

N-(Phosphonomethyl)-glycine is listed as glyphosate, $C_3H_8NO_5P$, molecular weight 169, in The Merck Index, 13$^{th}$ edition, 2001, page 803. The mono(isopropylamine) salt of N-(phosphonomethyl)-glycine is a primary active ingredient in Roundup® herbicide. N,N-Bis(phosphonomethyl)-glycine is listed as glyphosine, $C_4H_{11}NO_8P_2$, molecular weight 263, in The Merck Index, 13$^{th}$ edition, 2001, page 804. This compound is listed as plant growth regulator known to cause chlorosis in green plants, and also used as a chemical ripener. U.S. Pat. No. 3,288,846 entitled "Processes for Preparing Organo-Phosphonic Acids" describes a synthesis of N-substituted aminomethylenephosphonic acid. U.S. Pat. No. 3,799,758 entitled "N-Phosphonomethyl-Glycine Phytotoxicant Compositions" describes N-(phosphonomethyl)-glycine and its derivatives useful as phytotoxicants and herbicides. U.S. Pat. No. 3,853,530 entitled "Regulating Plants with N-phosphonomethyl-Glycine and Derivatives Thereof" describes the use of N-Phosphonomethyl-glycine and derivatives useful for regulating the natural growth and development of plants.

There has been no teaching, suggestion or implication about the use of N-(phosphonomethyl)-glycine or its derivatives for topical or systemic administration to mammals, including humans. The present inventors have determined that such compounds are useful for treating various medical and cosmetic conditions in animals, such as mammals, and including humans.

BRIEF SUMMARY OF THE INVENTION

One aspect of the present invention relates to an N-(phosphonoalkyl)-amino acid, a related compound or a derivative thereof, the N-(phosphonoalkyl)-amino acid, related compound or derivative thereof being in a form as a free acid, salt, partial salt, lactone, amide or ester, or in stereoisomeric or non-stereoisomeric form, other than N-(phosphonomethyl)-glycine or N,N-bis(phosphonomethyl)-glycine.

Another aspect of the present invention relates to an N-(phosphonoalkyl)-amino acid compound, a related compound or a compound derived therefrom, the compound includes the group consisting of N-(phosphonoalkyl)-proline and a compound or derivative thereof having the following formula:

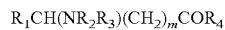

wherein $R_1$ is H, an alkyl group having 1 to 19 carbon atoms, an aryl group having 6 to 19 carbon atoms or an aralkyl group having 7 to 19 carbon atoms; and $R_1$ can also carry —OH, —SH, —SCH$_3$, —NH$_2$, —NR$_2$R$_3$, —COR$_4$, —NHCONH$_2$, —NHC(=NR$_2$)NH$_2$, imidazole, pyrrolidine or other heterocyclic group; m is an integer from 0 to 5; $R_2$ is a phosphonoalkyl group having a formula (HO)$_2$PO(CH$_2$)$_n$—; $R_3$ is H or a phosphonoalkyl group having a formula (HO)$_2$PO(CH$_2$)$_n$—; n is an integer from 1 to 9; $R_4$ is —NH$_2$ or —OR$_5$, $R_5$ is H, an alkyl group having 1 to 19 carbon atoms, an aryl group having 6 to 19 carbon atoms or an aralkyl group having 7 to 19 carbon atoms; and the H attached to any carbon atom can be substituted by I, F, Cl, Br, OH or an alkoxy group having 1 to 9 carbon atoms; and wherein the N-(phosphonoalkyl)-amino acid, related compound or derivative thereof is in a form as a free acid, salt, partial salt, lactone, amide or ester, or in a stereoisomeric or non-stereoisomeric form; provided that the compound is not N-(phosphonomethyl)-glycine or N,N-bis(phosphonomethyl)-glycine.

Another aspect of the present invention relates to a composition comprising an N-(phosphonoalkyl)-amino acid, a related compound or a derivative thereof, the N-(phosphonoalkyl)-amino acid, related compound or derivative thereof being in a form as a free acid, salt, partial salt, lactone, amide or ester, or in stereoisomeric or non-stereoisomeric form, and a cosmetically or pharmaceutically acceptable vehicle for topical or systemic administration to a mammalian subject.

Yet another aspect of the present invention relates to a method of alleviating or improving a condition, disorder, symptom or syndrome associated with at least one of a nervous, vascular, musculoskeletal or cutaneous system, the method comprising administering to a mammalian subject having the disorder, symptom or syndrome an amount effective for alleviating or improving the condition, disorder, symptom or syndrome of a composition comprising an N-(phosphonoalkyl)-amino acid, a related compound or a derivative thereof, the N-(phosphonoalkyl)-amino acid, related compound or derivative thereof being in a form as a free acid, salt, partial salt, lactone, amide or ester, or in stereoisomeric or non-stereoisomeric form, and a cosmetically or pharmaceutically acceptable vehicle for topical or systemic administration to the mammalian subject.

The cosmetic conditions and medical disorders, symptoms or syndromes associated with at least one of a nervous, vascular, musculoskeletal or cutaneous system, and others, include, by way of example and not limitation, itch, pain, inflammation, erythema, eczema, dermatitis, dermatoses, arthritis, acne, rosacea, dry skin, ichthyosis, keratoses, psoriasis, pigmented skin, aging related skin changes. The compositions may also be used for skin lightening.

As used herein, the singular forms "a", "an", and "the" include plural referents unless the context clearly dictates otherwise. Thus, for example, reference to "a compound" includes a plurality of such compounds.

DETAILED DESCRIPTION OF THE INVENTION

As noted above, the present invention relates to an N-(phosphonoalkyl)-amino acid, a related compound or a derivative thereof, the N-(phosphonoalkyl)-amino acid, related compound or derivative thereof being in a form as a free acid, salt, partial salt, lactone, amide or ester, or in stereoisomeric or non-stereoisomeric form, other than N-(phosphonomethyl)-glycine or N,N-bis(phosphonomethyl)-glycine.

Typical, but non-limiting phosphonoalkyl groups include phosphonomethyl, phosphonoethyl, phosphonopropyl, phosphonoisopropyl, phosphonobutyl, phosphonoisobutyl, phosphonopentyl, phosphonoisopentyl, phosphonooctyl and phosphonoisooctyl groups.

The present invention also relates to a composition including an N-(phosphonoalkyl)-amino acid, a related compound or a derivative thereof in a form as a free acid, salt, partial salt, lactone, amide or ester, or in stereoisomeric or non-stereoisomeric form, and a cosmetically or pharmaceutically acceptable vehicle for topical or systemic administration to a mammalian subject. The composition includes N-(phosphonoalkyl)-glycine, its related compounds and derivatives thereof, since they are not known for use in treating mammals, including humans.

The present invention additionally relates to a method of administering an effective amount of such a composition for alleviating or improving a condition, disorder, symptom or syndrome associated with at least one of a nervous, vascular, musculoskeletal or cutaneous system, or others.

The compositions comprising N-(phosphonoalkyl)-amino acids, preferably N-(phosphonomethyl)-amino acids, related compounds or derivatives thereof, and their topical or systemic administration to animals, such as mammals, including humans, are believed to be beneficial or therapeutically effective for cosmetic conditions or medical disorders associated with nervous, vascular, musculoskeletal, or cutaneous systems, or others.

The amino acid as used herein represents as a broad definition an organic compound which has at least one carboxyl group and at least one alkaline group such as amino, imino or guanidino group. The common amino acids represent twenty amino acids which have an amino group at the alpha position of the carbon chain and are present in proteins. These common amino acids are alanine, arginine, aspartic acid, asparagine, cysteine, glycine, glutamic acid, glutamine, histidine, isoleucine, leucine, lysine, methionine, phenylalanine, proline, serine, threonine, tryptophan, tyrosine and valine. From these common amino acids, twenty N-(phosphonoalkyl)-amino acids, preferably twenty N-(phosphonomethyl)-amino acids can be formed including different stereoisomers such as D, L and DL forms.

Some amino acids are metabolites or are related to or derived from the common amino acids. Other amino acids have amino group(s) at other positions of the carbon chain, such as the β or γ position. Still other amino acids are found in nature produced by microorganisms or plants. Certain amino acids, such as taurine, can have a sulfonic acid group instead of a carboxyl group. Peptides are derived from amino acids, and the peptides are called related amino acids or amino acid derivatives. Other organic compounds which have at least one carboxyl group and at least one alkaline group such as amino, imino or guanidino group are also called "related" amino acids. As used herein, all these compounds are called related amino acids. Representative, but non-limiting related amino acids include: β-alanine, γ-aminobutanoic acid, β-aminoisobutanoic acid, anserine, aminolevulinic acid, carnosine, canaline, canavanine, citrulline, creatine, creatinine, cysteine sulfinic acid, cystine, cycloserine, dopa (3,4-dihydroxyphenylalanine), dopamine (hydroxytyramine), ethionine, glutathione, guanidinoacetic acid, homocarnosine, homocysteine, homoserine, 4-hydroxyphenylglycine, hydroxyglutamic acid, hydroxylysine, hydroxyproline, hypusine, homoarginine, homocitrulline, homocystine, homophenylalanine, homotryptophan, hydroxylysine, hydroxyarginine, hydroxyhomoarginine, hydroxycitrulline, hydroxyornithine, hydroxyvaline, indospicine, methoxinine, methylarginine, methylhistidine, methyllysine, methylornithine, methylserine, norvaline, ornithine, oxalysine, penicillamine(dimethylcysteine), phenylglycine, 3-phenylserine, sarcosine (N-methylglycine), serotonin (hydroxytryptamine), taurine, tryptamine and tyramine.

As used herein, the N-(phosphonoalkyl) or preferably the N-(phosphonomethyl) derivatives of the amino acids as described in paragraphs [0016] and [0017] above, and certain others described elsewhere herein, are called "N-(phosphonoalkyl)-related amino acids," preferably "N-(phosphonomethyl)-related amino acids," or simply "related compounds" (or other similar grammatical terms). The "derivatives thereof" (or other similar grammatical forms) represent all other compounds which are chemically derived from the N-(phosphonoalkyl)-amino acids, the N-(phosphonoalkyl)-related amino acids, and preferably N-(phosphonomethyl)-amino acids and N-(phosphonomethyl)-related amino acids.

Conditions, disorders, symptoms and syndromes associated with the (A) nervous, (B) vascular, (C) masculoskeletal, (D) cutaneous system, and others that may be treated with a composition of the present invention can be described as follows.

(A) Nervous System.

Throughout this description, the conditions, disorders, symptoms and syndromes associated with the nervous system include the following conditions or disorders, which may present as indicated, or otherwise: (1) dementia and Alzheimer's disease: progressive loss of memory, shrinkage and atrophy of cerebral cortex, tangles of fibers in nerve cells, senile plaques of amyloid, decreased choline acetyltransferase enzyme; (2) carpal tunnel syndrome: weakness, pain, tingling, numbness, burning in palm and fingers; (3) encephalitis: inflammation of the brain; (4) headache: migraine, expansion of blood vessels pressing on nerves or constriction blocking blood supply, inflammation, muscle contraction to face, neck or scalp; (5) meningitis: infection of spinal fluid and meninges; (6) neuralgia: nerve pain, peripheral neuropathy, sciatica, shingles, trigeminal neuralgia; (7) Parkinson's disease: tremors in limbs, muscular rigidity; (8) amnesia: loss of memory and inability to form new memory; and (9) others, such as ataxia, Bell's palsy, epilepsy, multiple sclerosis, myasthenia gravis, narcolepsy, paralysis and rabies.

(B) Vascular System.

Throughout this description, vascular conditions, reactions and disorders that may be treated with a composition of the present invention include acanthosis nigricans, acrocyanosis, actinic cheilitis, actinic prurigo, dermatitis, dermatosis, dermographism, dyshidrosis, drug eruptions, eczema, erythema, erythema migrans, erythrocyanosis, erythromelalgia, familial hemorrhage, histamine reaction, inflammatory papular and pustular lesions, lichen planus, lupus erythematosus, mycosis fungoides, neurodermatitis, neuropeptide and neurovascular reactions, parapsoriasis, perniosis (chilblains), photoallergy, photoreaction, photosensitivity, pityriasis rosea, pityriasis rubra pilaris, polymorphic light eruption, psoriasis, rhinophyma, rosacea, sclerosis, spider naevi, T-cell disorders, telangiectasia, urticaria and other vascular reactions.

(C) Musculoskeletal System.

The conditions or abnormalities of musculoskeletal system include the following conditions or disorders, which may present as indicated, or otherwise: (1) osteoporosis: reduction of calcium in bone leading to thin bone and bone susceptible to fracture; (2) osteoarthritis: inflammation of joint cartilage provoking swelling and pain; (3) rheumatoid arthritis: inflammation of synovium and destruction of cartilage, damage to heart, lungs, nerves and eyes; (4) ankylosing spondylitis: arthritis affecting sacroiliac joints and spine with inflammation and immovability; (5) bursitis: inflammation of bursa; (6) tendinitis: inflammation of tendon; (7) gout: recurrent acute arthritis from uric acid deposit; and (8) others, such as backache, bunion and hernia.

(D) Cutaneous System, and Others.

The cosmetic, dermatological or other conditions and disorders of cutaneous system that my be treated with a composition of the present invention include deranged or disordered cutaneous or mucocutaneous tissue relevant to skin, nail and hair; oral, vaginal and anal mucosa; disturbed keratinization; inflammation; changes associated with intrinsic and extrinsic aging, and others which may or may not be related to cutaneous system. The manifestations include acne; rosacea; age spots; blemished skin; blotches; cellulite; dermatoses; dermatitis; skin, nail and hair infections; dandruff; dryness or looseness of skin, nail and hair; xerosis; eczema; elastosis; herpes; hyperkeratosis; hyperpigmented skin; ichthyosis; keratoses; lentigines; melasmas; mottled skin; pseudofolliculitis barbae; photoaging and photodamage; pruritus; psoriasis; skin lines; stretch marks; thinning of skin, nail plate and hair; warts; wrinkles; oral or gum disease; irritated, inflamed, red, unhealthy, damaged or abnormal mucosa, skin, hair, nail, nostril, ear canal, anal or vaginal conditions; breakdown, defective synthesis or repair of dermal components; abnormal or diminished synthesis of collagen, glycosaminoglycans, proteoglycans and elastin, as well as diminished levels of such components in the dermis; uneven skin tone; uneven and rough surface of skin, nail and hair; loss or reduction of skin, nail and hair resiliency, elasticity and recoilability; laxity; lack of skin, nail and hair lubricants and luster; fragility and splitting of nail and hair; yellowing skin; reactive, irritating or telangiectatic skin; and dull and older-looking skin, nail and hair. In addition, N-(phosphonoalkyl)-amino acids can be used for general care of skin, nail and hair; to improve skin texture and pores, flakiness and redness; to make skin soft, smooth, fresh, balanced, visibly clear, even-toned and brighter; to increase skin fullness and plumpness; and for skin bleach and lightening and wound healing.

Skin, nail and hair infections can be caused by microorganisms which include bacteria, fungi, yeasts, molds, parasites and viruses. More specifically, the bacterial infections can cause trichomycosis axillaris, pitted keratolysis, erythrasma, impetigo, eethyma, furunculosis (boils), carbuncle, scalded skin syndrome, toxic shock syndrome, erysipelas, cellulitis, necrotizing fasciitis, erysipeloid, cat-scratch disease (*Rochalimaea henselae*), syphilis, lyme disease (*Borrelia burgdorferi*), cutaneous anthrax (*Bacillus anthracis*), gonococcal septicaemia, inoculation tuberculosis, scrofuloderma, tuberculides, erythema induratum, leprosy (*Mycobacterium leprae*), mycobacterium ulcerans, leishmaniasis and acute paronychia. The viral infections can cause viral warts (human papilloma virus), varicella (chickenpox), herpes zoster (varicella-zoster), herpes simplex (herpesvirus hominis), molluscum contagiosum, orf, AIDS (acquired immunodeficiency syndrome, human immunodeficiency virus, HIV), herpangina, mucocutaneous lymph node syndrome (Kawasaki's disease), Gianotti-Crosti syndrome (hepatitis B virus), measles, rubella and erythema infectiosum. The fungal infections can cause ringworm, tinea pedis (athlete's foot), tinea nails, tinea hands, tinea groin, tinea trunk and limbs, tinea capitis (scalp), oral candidiasis, candida intertrigo, genital candidiasis, chronic paronychia, chronic mucocutaneous candidiasis, pityriasis versicolor, histoplasmosis, coccidioidomycosis, blastomycosis, sporotrichosis, actinomycosis and mycetoma (madura foot).

The systemic administration includes parenteral injection, such as intravenous or intraarterial injection or infusion, subcutaneous, intramuscular or other injection, as well as oral, transdermal and other routes. The preferred systemic administration is oral administration.

Certain N-(phosphonoalkyl)-amino acids, related compounds and derivatives thereof can be represented by the following generic formula:

$R_1CH(NR_2R_3)(CH_2)_mCOR_4$ wherein $R_1$ is H, an alkyl group having 1 to 19 carbon atoms, an aryl group having 6 to 19 carbon atoms or an aralkyl group having 7 to 19 carbon atoms; and $R_1$ can also carry —OH, —SH, —SCH$_3$, —NH$_2$, —NR$_2$R$_3$, —COR$_4$, —NHCONH$_2$, —NHC(=NR$_2$)NH$_2$, imidazole, pyrrolidine or other heterocyclic group; m is an integer from 0 to 5; $R_2$ is a phosphonoalkyl group having a formula $(HO)_2PO(CH_2)_n$—; $R_3$ is H or a phosphonoalkyl group having a formula $(HO)_2PO(CH_2)_n$—; n is an integer from 1 to 9; $R_4$ is —NH$_2$ or —OR$_5$, $R_5$ is H, an alkyl group having 1 to 19 carbon atoms, an aryl group having 6 to 19 carbon atoms or an aralkyl group having 7 to 19 carbon atoms; and the H attached to any carbon atom can be substituted by I, F, Cl, Br, OH or an alkoxy group having 1 to 9 carbon atoms. Typical, but non-limiting phosphonoalkyl groups include phosphonomethyl, phosphonoethyl, phosphonopropyl, phosphonoisopropyl, phosphonobutyl, phosphonoisobutyl, phosphonopentyl, phosphonoisopentyl, phosphonooctyl and phosphonoisooctyl groups. The most preferred one is phosphonomethyl group. The N-(phosphonoalkyl)-amino acid, related compound or derivative thereof can be present in a form as free acid, salt or partial salt with organic or inorganic alkali, amide, ester or lactone, as a stereoisomer such as in D, L, or DL form, or as a non-stereoisomer such as N-(phosphonoalkyl)-β-alanine. Among N-(phosphonoalkyl)-amino acids, N-(phosphonoalkyl)-proline cannot be represented by the above generic structure because the α-amino group is part of the heterocyclic pyrrolidine ring. Therefore, N-(phosphonoalkyl) derivatives of proline such as N-(phosphonoalkyl)-proline, N-(phosphonoalkyl)-prolinamide and N-(phosphonoalkyl)-proline esters will be represented by their chemical names. In the same manner, chemical names will be used if other compounds of the present invention cannot be covered by the above generic structure.

Each of the amino groups of an amino acid excluding proline has two hydrogen atoms attached to the nitrogen atom, and can form a bis or di(phosphonoalkyl)-amino acid such as N,N-bis(phosphonoalkyl)-alanine and N,N-bis(phosphonoalkyl)-tyrosine.

Most amino acids and related amino acids have only one amino group attached to the alpha or other position of the carbon atom, and can have only one or two (phosphonoalkyl) groups attached to the amino group such as N-(phosphonoalkyl)-serine and N,N-bis(phosphonoalkyl)-serine. Some amino acids and related amino acids, such as lysine, ornithine, arginine, histidine and tryptophan have additional amino, imino or guanidino groups in addition to the alpha amino group, and can form one to four (phosphonoalkyl) groups, for example: N-(phosphonoalkyl)-amino acids; N'-(phosphonoalkyl)-amino acids; N,N-bis(phosphonoalkyl)-amino acids; N,N'-bis(phosphonoalkyl)-amino acids; N',N'-bis(phosphonoalkyl)-amino acids; N,N,N'-tris(phosphonoalkyl)-amino acids; N,N',N'-tris(phosphonoalkyl)-amino acids and N,N,N',N'-tetra(phosphonoalkyl)-amino acids. Non-limiting examples are N-(phosphonoalkyl)-lysine; N'-(phosphonoalkyl)-lysine; N,N-bis(phosphonoalkyl)-lysine; N,N'-bis(phosphonoalkyl)-lysine; N',N'-bis(phosphonoalkyl)-lysine; N,N,N'-tris(phosphonoalkyl)-lysine; N,N',N'-tris(phosphonoalkyl)-lysine and N,N,N',N'-tetra(phosphonoalkyl)-lysine. All of the foregoing are to be included as "related compounds" or "derivatives."

A more preferred N-(phosphonoalkyl) compound has a single phosphonoalkyl radical attached to an amino group of an amino acid or related amino acid, such as alpha N-(phosphonoalkyl)-lysine and N-(phosphonoalkyl)-γ-aminobutanoic acid.

Representative non-limiting mono-substituted common amino acids include:

N-(phosphonoalkyl)-alanine, N-(phosphonoalkyl)-arginine, N-(phosphonoalkyl)-asparagine, N-(phosphonoalkyl)-aspartic acid, N-(phosphonoalkyl)-cysteine, N-(phosphonoalkyl)-glycine, N-(phosphonoalkyl)-glutamic acid, N-(phosphonoalkyl)-glutamine, N-(phosphonoalkyl)-histidine, N-(phosphonoalkyl)-isoleucine, N-(phosphonoalkyl)-leucine, N-(phosphonoalkyl)-lysine, N-(phosphonoalkyl)-methionine, N-(phosphonoalkyl)-phenylalanine, N-(phosphonoalkyl)-proline, N-(phosphonoalkyl)-serine, N-(phosphonoalkyl)-threonine, N-(phosphonoalkyl)-tryptophan, N-(phosphonoalkyl)-tyrosine and N-(phosphonoalkyl)-valine.

Representative, non-limiting mono-substituted related amino acids include:

N-(phosphonoalkyl)-β-alanine, N-(phosphonoalkyl)-γ-aminobutanoic acid, N-(phosphonoalkyl)-β-aminoisobutanoic acid, N-(phosphonoalkyl)-anserine, N-(phosphonoalkyl)-aminolevulinic acid, N-(phosphonoalkyl)-carnosine, N-(phosphonoalkyl)-canaline, N-(phosphonoalkyl)-canavanine, N-(phosphonoalkyl)-citrulline, N-(phosphonoalkyl)-creatine, N-(phosphonoalkyl)-creatinine, N-(phosphonoalkyl)-cysteine sulfinic acid, N-(phosphonoalkyl)-cystine, N-(phosphonoalkyl)-cycloserine, N-(phosphonoalkyl)-dopa[N-(phosphonoalkyl)-3,4-dihydroxyphenylalanine], N-(phosphonoalkyl)-dopamine (hydroxytyramine), N-(phosphonoalkyl)-ethionine, N-(phosphonoalkyl)-glutathione, N-(phosphonoalkyl)-guanidinoacetic acid, N-(phosphonoalkyl)-3-guanidinopropanoic acid, N-(phosphonoalkyl)-4-guanidinobutanoic acid, N-(phosphonoalkyl)-homocarnosine, N-(phosphonoalkyl)-homocysteine, N-(phosphonoalkyl)-homoserine, N-(phosphonoalkyl)-4-hydroxyphenylglycine, N-(phosphonoalkyl)-hydroxyglutamic acid, N-(phosphonoalkyl)-hydroxylysine, N-(phosphonoalkyl)-hydroxyproline, N-(phosphonoalkyl)-hypusine, N-(phosphonoalkyl)-homoarginine, N-(phosphonoalkyl)-homocitrulline, N-(phosphonoalkyl)-homocystine, N-(phosphonoalkyl)-homophenylalanine, N-(phosphonoalkyl)-homotryptophan, N-(phosphonoalkyl)-hydroxylysine, N-(phosphonoalkyl)-hydroxyarginine, N-(phosphonoalkyl)-hydroxyhomoarginine, N-(phosphonoalkyl)-hydroxycitrulline, N-(phosphonoalkyl)-hydroxyornithine, N-(phosphonoalkyl)-hydroxyvaline, (phosphonoalkyl)-iminodiacetic acid, N-(phosphonoalkyl)-indospicine, N-(phosphonoalkyl)-methoxinine, N-(phosphonoalkyl)-methylarginine, N-(phosphonoalkyl)-methylhistidine, N-(phosphonoalkyl)-methyllysine, N-(phosphonoalkyl)-methylornithine, N-(phosphonoalkyl)-methylserine, N-(phosphonoalkyl)-norvaline, N-(phosphonoalkyl)-ornithine, N-(phosphonoalkyl)-oxalysine, N-(phosphonoalkyl)-penicillamine(N-phosphonoalkyl-dimethylcysteine), N-(phosphonoalkyl)-phenylglycine, N-(phosphonoalkyl)-3-phenylserine, N-(phosphonoalkyl)-sarcosine (N-phosphonoalkyl-N-methyl-glycine), N-(phosphonoalkyl)-serotonin (N-phosphonoalkyl-hydroxytryptamine), N-(phosphonoalkyl)-taurine, N-(phosphonoalkyl)-tryptamine and N-(phosphonoalkyl)-tyramine.

Representative, non-limiting di- or bis-substituted amino acids include:

N,N-bis(phosphonoalkyl)-alanine; N,N-bis(phosphonoalkyl)-arginine; N,N-bis(phosphonoalkyl)-asparagine; N,N-bis(phosphonoalkyl)-aspartic acid; N,N-bis(phosphonoalkyl)-cysteine; N,N-bis(phosphonoalkyl)-glycine; N,N-bis(phosphonoalkyl)-glutamic acid; N,N-bis(phosphonoalkyl)-glutamine; N,N-bis(phosphonoalkyl)-histidine; N,N-bis(phosphonoalkyl)-isoleucine; N,N-bis(phosphonoalkyl)-leucine; N,N-bis(phosphonoalkyl)-lysine; N,N-bis(phosphonoalkyl)-methionine; N,N-bis(phosphonoalkyl)-phenylalanine; N,N-bis(phosphonoalkyl)-serine; N,N-bis(phosphonoalkyl)-threonine; N,N-bis(phosphonoalkyl)-tryptophan; N,N-bis(phosphonoalkyl)-tyrosine; N,N-bis(phosphonoalkyl)-valine; N,N'-bis(phosphonoalkyl)-arginine; N,N'-bis(phosphonoalkyl)-histidine; N,N'-bis(phosphonoalkyl)-lysine; N,N'-bis(phosphonoalkyl)-tryptophan. These di- or bis-substituted amino acids are within the category of derivatives of amino acids.

Representative non-limiting di- or bis-substituted related amino acids and derivatives include:

N,N-bis(phosphonoalkyl)-β-alanine; N,N-bis(phosphonoalkyl)-γ-aminobutanoic acid; N,N-bis(phosphonoalkyl)-α-aminoisobutanoic acid; N,N-bis(phosphonoalkyl)-anserine; N,N-bis(phosphonoalkyl)-aminolevulinic acid; N,N-bis(phosphonoalkyl)-carnosine; N,N-bis(phosphonoalkyl)-canaline; N,N-bis(phosphonoalkyl)-canavanine; N,N-bis(phosphonoalkyl)-citrulline; N,N-bis(phosphonoalkyl)-creatine; N,N-bis(phosphonoalkyl)-creatinine; N,N-bis(phosphonoalkyl)-cysteine sulfinic acid; N,N-bis(phosphonoalkyl)-cystine; N,N-bis(phosphonoalkyl)-cycloserine; N,N-bis(phosphonoalkyl)-dopa[N,N-bis(phosphonoalkyl)-3,4-dihydroxyphenylalanine]; N,N-bis(phosphonoalkyl)-dopamine(hydroxytyramine); N,N-bis(phosphonoalkyl)-ethionine; N,N-bis(phosphonoalkyl)-glutathione; N,N-bis(phosphonoalkyl)-guanidinoacetic acid; N,N-bis(phosphonoalkyl)-3-guanidinopropanoic acid; N,N-bis(phosphonoalkyl)-4-guanidinobutanoic acid; N,N-bis(phosphonoalkyl)-homocarnosine; N,N-bis(phosphonoalkyl)-homocysteine; N,N-bis(phosphonoalkyl)-homoserine; N,N-bis(phosphonoalkyl)-4-hydroxyphenylglycine; N,N-bis(phosphonoalkyl)-hydroxyglutamic acid; N,N-bis(phosphonoalkyl)-hydroxylysine; N,N-bis(phosphonoalkyl)-hydroxyproline;

N,N-bis(phosphonoalkyl)-hypusine; N,N-bis(phosphonoalkyl)-homoarginine; N,N-bis(phosphonoalkyl)-homocitrulline; N,N-bis(phosphonoalkyl)-homocystine; N,N-bis(phosphonoalkyl)-homophenylalanine; N,N-bis(phosphonoalkyl)-homotryptophan; N,N-bis(phosphonoalkyl)-hydroxylysine; N,N-bis(phosphonoalkyl)-hydroxyarginine; N,N-bis(phosphonoalkyl)-hydroxyhomoarginine; N,N-bis(phosphonoalkyl)-hydroxycitrulline; N,N-bis(phosphonoalkyl)-hydroxyornithine; N,N-bis(phosphonoalkyl)-hydroxyvaline; N,N-bis(phosphonoalkyl)-indospicine; N,N-bis(phosphonoalkyl)-methoxinine; N,N-bis(phosphonoalkyl)-methylarginine; N,N-bis(phosphonoalkyl)-methylhistidine; N,N-bis(phosphonoalkyl)-methyllysine; N,N-bis(phosphonoalkyl)-methylornithine; N,N-bis(phosphonoalkyl)-methylserine; N,N-bis(phosphonoalkyl)-norvaline; N,N-bis(phosphonoalkyl)-ornithine; N,N-bis(phosphonoalkyl)-oxalysine; N,N-bis(phosphonoalkyl)-penicillamine (N-phosphonoalkyl-dimethylcysteine); N,N-bis(phosphonoalkyl)-phenylglycine; N,N-bis(phosphonoalkyl)-3-phenylserine; N,N-bis(phosphonoalkyl)-serotonin (N-phosphonoalkyl-hydroxytryptamine); N,N-bis(phosphonoalkyl)-taurine; N,N-bis(phosphonoalkyl)-tryptamine and N,N-bis(phosphonoalkyl)-tyramine. These di- or bis-substituted related amino acids are included with the invention as derivatives of related amino acids.

Any of the above phosphonoalkyl-amino acids, related compounds and derivatives thereof can be present as a free acid, salt or partial salt with organic or inorganic alkali, lactone, amide, ester or in stereoisomeric or non-stereoisomeric form.

As an illustration, N-(phosphonoalkyl)-proline includes for example, N-(phosphonoalkyl)-L-proline; N-(phosphonoalkyl)-L-proline sodium salt; N-(phosphonoalkyl)-L-prolinamide, N-(phosphonoalkyl)-L-proline methyl ester, N-(phosphonoalkyl)-L-proline ethyl ester, N-(phosphonoalkyl)-L-proline propyl ester and N-(phosphonoalkyl)-L-proline isopropyl ester.

The preferred phosphonoalkyl groups are phosphonomethyl, phosphonoethyl, phosphonopropyl, phosphonoisopropyl, phosphonobutyl, phosphonoisobutyl, phosphonopentyl, phosphonoisopentyl, phosphonooctyl and phosphonoisooctyl groups. Therefore, the preferred compounds of the present invention are N-(phosphonomethyl)-amino acids, N-(phosphonoethyl)-amino acids, N-(phosphonopropyl)-amino acids, N-(phosphonoisopropyl)-amino acids, N-(phosphonobutyl)-amino acids, N-(phosphonoisobutyl)-amino acids, N-(phosphonopentyl)-amino acids, N-(phosphonoisopentyl)-amino acids, N-(phosphonooctyl)-amino acids, N-(phosphonoisooctyl)-amino acids, and the related amino acid compounds and derivatives thereof. The most preferred compounds are N-(phosphonomethyl)-amino acids, related compounds and derivatives thereof, in which $R_2$ is a (phosphonomethyl) group having the formula $(HO)_2PO(CH_2)$, and $R_3$ is H or a phosphonomethyl group having the formula $(HO)_2PO(CH_2)$ in the above generic structure.

Among N-(phosphonomethyl)-amino acids, N-(phosphonomethyl)-proline cannot be represented by the above generic structure because the alpha amino group is part of the heterocyclic pyrrolidine ring. Therefore, N-(phosphonomethyl) derivatives of proline such as N-(phosphonomethyl)-proline, N-(phosphonomethyl)-prolinamide and N-(phosphonomethyl)-proline esters will be represented by their chemical names. In the same manner, chemical names will be used if other compounds of the present invention cannot be covered by the above generic structure.

As aforementioned, each of any of the amino groups of an amino acid excluding proline has two hydrogen atoms attached to the nitrogen atom, and can form bis- or di-(phosphonomethyl)-amino acid such as N,N-bis(phosphonomethyl)-cysteine and N,N-bis(phosphonomethyl)-leucine. Most amino acids and related amino acids have only one amino group attached to the alpha or other position of the carbon atom, and can have only one or two (phosphonomethyl) groups attached to the amino group such as N-(phosphonomethyl)-serine and N,N-bis(phosphonomethyl)-serine. Some amino acids and related amino acids, such as lysine, ornithine, arginine, histidine and tryptophan have additional amino, imino or guanidino group in addition to the alpha amino group, and can form one to four (phosphonomethyl) groups, such as N-(phosphonomethyl)-amino acids; N'-(phosphonomethyl)-amino acids; N,N-bis(phosphonomethyl)-amino acids; N,N'-bis(phosphonomethyl)-amino acids; N'N'-bis(phosphonomethyl)-amino acids; N,N,N'-tris(phosphonomethyl)-amino acids; N,N'N'-tris(phosphonomethyl)-amino acids and N,N,N'N'-tetra(phosphonomethyl)-amino acids. Non-limiting examples are N-(phosphonomethyl)-lysine; N'-(phosphonomethyl)-lysine; N,N-bis(phosphonomethyl)-lysine; N,N'-bis(phosphonomethyl)-lysine; N',N'-bis(phosphonomethyl)-lysine; N,N,N'-tris(phosphonomethyl)-lysine; N,N'N'-tris(phosphonomethyl)-lysine and N,N,N'N'-tetra(phosphonomethyl)-lysine. A presently more preferred N-(phosphonomethyl) derivative is a single phosphonomethyl radical attached to an amino group of an amino acid or related amino acid, such as alpha N-(phosphonomethyl)-lysine and N-(phosphonomethyl)-γ-aminobutanoic acid.

The preferred mono-substituted common amino acids include:

N-(phosphonomethyl)-alanine, N-(phosphonomethyl)-arginine, N-(phosphonomethyl)-asparagine, N-(phosphonomethyl)-aspartic acid, N-(phosphonomethyl)-cysteine, N-(phosphonomethyl)-glycine, N-(phosphonomethyl)-glutamic acid, N-(phosphonomethyl)-glutamine, N-(phosphonomethyl)-histidine, N-(phosphonomethyl)-isoleucine, N-(phosphonomethyl)-leucine, N-(phosphonomethyl)-lysine, N-(phosphonomethyl)-methionine, N-(phosphonomethyl)-phenylalanine, N-(phosphonomethyl)-proline, N-(phosphonomethyl)-serine, N-(phosphonomethyl)-threonine, N-(phosphonomethyl)-tryptophan, N-(phosphonomethyl)-tyrosine and N-(phosphonomethyl)-valine. These are within the category of N-(phosphonomethyl)-amino acids.

The preferred mono-substituted related amino acids include:

N-(phosphonomethyl)-β-alanine, N-(phosphonomethyl)-γ-aminobutanoic acid, N-(phosphonomethyl)-β-aminoisobutanoic acid, N-(phosphonomethyl)-anserine, N-(phosphonomethyl)-aminolevulinic acid, N-(phosphonomethyl)-carnosine, N-(phosphonomethyl)-canaline, N-(phosphonomethyl)-canavanine, N-(phosphonomethyl)-citrulline, N-(phosphonomethyl)-creatine, N-(phosphonomethyl)-creatinine, N-(phosphonomethyl)-cysteine sulfinic acid, N-(phosphonomethyl)-cystine, N-(phosphonomethyl)-cycloserine, N-(phosphonomethyl)-dopa [N-(phosphonomethyl)-3,4-dihydroxyphenylalanine], N-(phosphonomethyl)-dopamine(hydroxytyramine), N-(phosphonomethyl)-ethionine, N-(phosphonomethyl)-glutathione, N-(phosphonomethyl)-guanidinoacetic acid, N-(phosphonomethyl)-3-guanidinopropanoic acid, N-(phosphonomethyl)-4-guanidinobutanoic acid, N-(phosphonomethyl)-homocamosine, N-(phosphonomethyl)-homocysteine, N-(phosphonomethyl)-homoserine, N-(phosphonomethyl)-

4-hydroxyphenylglycine, N-(phosphonomethyl)-hydroxyglutamic acid, N-(phosphonomethyl)-hydroxylysine, N-(phosphonomethyl)-hydroxyproline, N-(phosphonomethyl)-hypusine, N-(phosphonomethyl)-homoarginine, N-(phosphonomethyl)-homocitrulline, N-(phosphonomethyl)-homocystine, N-(phosphonomethyl)-homophenylalanine, N-(phosphonomethyl)-homotryptophan, N-(phosphonomethyl)-hydroxylysine, N-(phosphonomethyl)-hydroxyarginine, N-(phosphonomethyl)-hydroxyhomoarginine, N-(phosphonomethyl)-hydroxycitrulline, N-(phosphonomethyl)-hydroxyornithine, N-(phosphonomethyl)-hydroxyvaline, N-(phosphonomethyl)iminodiacetic acid, N-(phosphonomethyl)-indospicine, N-(phosphonomethyl)-methoxinine, N-(phosphonomethyl)-methylarginine, N-(phosphonomethyl)-methylhistidine, N-(phosphonomethyl)-methyllysine, N-(phosphonomethyl)-methylornithine, N-(phosphonomethyl)-methylserine, N-(phosphonomethyl)-norvaline, N-(phosphonomethyl)-ornithine, N-(phosphonomethyl)-oxalysine, N-(phosphonomethyl)-penicillamine(N-phosphonomethyl-dimethylcysteine), N-(phosphonomethyl)-phenylglycine, N-(phosphonomethyl)-3-phenylserine, N-(phosphonomethyl)-sarcosine (N-phosphonomethyl-N-methyl-glycine), N-(phosphonomethyl)-serotonin (N-phosphonomethyl-hydroxytryptamine), N-(phosphonomethyl)-taurine, N-(phosphonomethyl)-tryptamine and N-(phosphonomethyl)-tyramine. These compounds are within the category of N-(phosphonomethyl)-related amino acids, or simply, related compounds.

The preferred di- or bis-substituted common amino acids are:

N,N-bis(phosphonomethyl)-alanine; N,N-bis(phosphonomethyl)-arginine; N,N-bis(phosphonomethyl)-aspartic acid; N,N-bis(phosphonomethyl)-asparagines; N,N-bis(phosphonomethyl)-cysteine; N,N-bis(phosphonomethyl)-glycine; N,N-bis(phosphonomethyl)-glutamic acid; N,N-bis(phosphonomethyl)-glutamine; N,N-bis(phosphonomethyl)-histidine; N,N-bis(phosphonomethyl)-isoleucine; N,N-bis(phosphonomethyl)-leucine; N,N-bis(phosphonomethyl)-lysine; N,N-bis(phosphonomethyl)-methionine; N,N-bis(phosphonomethyl)-phenylalanine; N,N-bis(phosphonomethyl)-serine; N,N-bis(phosphonomethyl)-threonine; N,N-bis(phosphonomethyl)-tryptophan; N,N-bis(phosphonomethyl)-tyrosine; N,N-bis(phosphonomethyl)-valine; N,N'-bis(phosphonomethyl)-arginine; N,N'-bis(phosphonomethyl)-histidine; N,N'-bis(phosphonomethyl)-lysine and N,N'-bis(phosphonomethyl)-tryptophan. These compounds are within the category of derivatives.

The preferred di- or bis-substituted related amino acids and derivatives include:

N,N-bis(phosphonomethyl)-β-alanine; N,N-bis(phosphonomethyl)-γ-aminobutanoic acid; N,N-bis(phosphonomethyl)-β-aminoisobutanoic acid; N,N-bis(phosphonomethyl)-anserine; N,N-bis(phosphonomethyl)-aminolevulinic acid; N,N-bis(phosphonomethyl)-carnosine; N,N-bis(phosphonomethyl)-canaline; N,N-bis(phosphonomethyl)-canavanine; N,N-bis(phosphonomethyl)-citrulline; N,N-bis(phosphonomethyl)-creatine; N,N-bis(phosphonomethyl)-creatinine; N,N-bis(phosphonomethyl)-cysteine sulfinic acid; N,N-bis(phosphonomethyl)-cystine; N,N-bis(phosphonomethyl)-cycloserine; N,N-bis(phosphonomethyl)-dopa(3; N,N-bis(phosphonomethyl)-4-dihydroxyphenylalanine); N,N-bis(phosphonomethyl)-dopamine(hydroxytyramine); N,N-bis(phosphonomethyl)-ethionine; N,N-bis(phosphonomethyl)-glutathione; N,N-bis(phosphonomethyl)-guanidinoacetic acid; N,N-bis(phosphonomethyl)-3-guanidinopropanoic acid; N,N-bis(phosphonomethyl)-4-guanidinobutanoic acid; N,N-bis(phosphonomethyl)-homocarnosine; N,N-bis(phosphonomethyl)-homocysteine; N,N-bis(phosphonomethyl)-homoserine; N,N-bis(phosphonomethyl)-4-hydroxyphenylglycine; N,N-bis(phosphonomethyl)-hydroxyglutamic acid; N,N-bis(phosphonomethyl)-hydroxylysine; N,N-bis(phosphonomethyl)-hydroxyproline; N,N-bis(phosphonomethyl)-hypusine; N,N-bis(phosphonomethyl)-homoarginine; N,N-bis(phosphonomethyl)-homocitrulline; N,N-bis(phosphonomethyl)-homocystine; N,N-bis(phosphonomethyl)-homophenylalanine; N,N-bis(phosphonomethyl)-homotryptophan; N,N-bis(phosphonomethyl)-hydroxylysine; N,N-bis(phosphonomethyl)-hydroxyarginine; N,N-bis(phosphonomethyl)-hydroxyhomoarginine; N,N-bis(phosphonomethyl)-hydroxycitrulline; N,N-bis(phosphonomethyl)-hydroxyornithine; N,N-bis(phosphonomethyl)-hydroxyvaline; N,N-bis(phosphonomethyl)-indospicine; N,N-bis(phosphonomethyl)-methoxinine; N,N-bis(phosphonomethyl)-methylarginine; N,N-bis(phosphonomethyl)-methylhistidine; N,N-bis(phosphonomethyl)-methyllysine; N,N-bis(phosphonomethyl)-methylornithine; N,N-bis(phosphonomethyl)-methylserine; N,N-bis(phosphonomethyl)-norvaline; N,N-bis(phosphonomethyl)-ornithine; N,N-bis(phosphonomethyl)-oxalysine; N,N-bis(phosphonomethyl)-penicillamine(N-phosphonomethyl-dimethylcysteine); N,N-bis(phosphonomethyl)-phenylglycine; N,N-bis(phosphonomethyl)-3-phenylserine; N,N-bis(phosphonomethyl)-sarcosine (N-phosphonomethyl-N-methyl-glycine); N,N-bis(phosphonomethyl)-serotonin (N-phosphonomethyl-hydroxytryptamine); N,N-bis(phosphonomethyl)-taurine; N,N-bis(phosphonomethyl)-tryptamine; N,N-bis(phosphonomethyl)-tyramine and N,N'-bis(phosphonomethyl)-ornithine. These compounds are within the category of derivatives.

Any of the above phosphonomethyl-amino acids, related compounds and derivatives thereof can be present as a free acid, salt, or partial salt with organic or inorganic alkali, lactone, amide, ester or in stereoisomeric or non-stereoisomeric form.

As an illustration, N-(phosphonomethyl)-proline includes for example, N-(phosphonomethyl)-L-proline; N-(phosphonomethyl)-L-proline sodium salt; N-(phosphonomethyl)-L-prolinamide, N-(phosphonomethyl)-L-proline methyl ester, N-(phosphonomethyl)-L-proline ethyl ester, N-(phosphonomethyl)-L-proline propyl ester and N-(phosphonomethyl)-L-proline isopropyl ester.

Synthesis of N-(Phosphonomethyl)-Amino Acids and Related Compounds

Among different syntheses, the most convenient and simplest method is the following process which is modified from the examples described in U.S. Pat. No. 3,799,758, the disclosure of which is hereby incorporated by reference herein.

In general, most N-(phosphonomethyl)-amino acids and related compounds can be synthesized by the following exemplary, non-limiting method.

An amino acid (1.1 mole) and chloromethyl phosphonic acid (1 mole) in 300 ml of 8N NaOH were heated at 100° C. for 24 hours. After the reaction mixture was cooled to room temperature, 250 ml of 12N HCl was slowly added with stirring while the container was cooled externally with a cold-water bath. The mixture was filtered, and the filtrate was cooled with an ice-water bath. From the filtrate, N-(phosphonomethyl)-amino acid was obtained as a precipitate which was washed with cold dilute HCl and cold water. The product thus obtained was identified by routine chemical methods.

The ester form of an N-(phosphonomethyl)-amino acid was synthesized by a conventional process which included heating the N-(phosphonomethyl)-amino acid in anhydrous alcohol containing HCl gas. Methyl, ethyl, propyl and isopropyl esters of an N-(phosphonomethyl)-amino acid were readily synthesized by the above simple process. For example, N-(phosphonomethyl)-L-proline ethyl ester, N-(phosphonomethyl)-L-tyrosine ethyl ester, N-(phosphonomethyl)-D-4-hydroxyphenylglycine ethyl ester, N-(phosphonomethyl)-glycine propyl ester and N-(phosphonomethyl)-glycine isopropyl ester were synthesized from their correspondent N-(phosphonomethyl)-amino acids by the above process.

The amide form of an N-(phosphonomethyl)-amino acid was also synthesized by a conventional process which included reaction of an N-(phosphonomethyl)-amino acid methyl ester with ammonia gas in anhydrous methanol. For example, N-(phosphonomethyl)-glycinamide was synthesized from N-(phosphonomethyl)-glycine methyl ester by the above process.

The N-(phosphonoalkyl)-amino acids and related compounds can be synthesized by the same procedure except that chloromethyl phosphonic acid is replaced by chloroalkyl phosphonic acid.

By using the above process the following specific N-(phosphonomethyl)-amino acids and related compounds have been synthesized:

N-(phosphonomethyl)-asparagine, N-(phosphonomethyl)-cysteine, N-(phosphonomethyl)-glycine, N-(phosphonomethyl)-glutamic acid, N-(phosphonomethyl)-glutamine, N-(phosphonomethyl)-proline, N-(phosphonomethyl)-serine, N-(phosphonomethyl)-tyrosine, N-(phosphonomethyl)-γ-aminobutanoic acid, N-(phosphonomethyl)-creatine, N-(phosphonomethyl)-creatinine, N-(phosphonomethyl)-glutathione, N-(phosphonomethyl)-4-hydroxyphenylglycine, N-(phosphonomethyl)-ornithine, and N-(phosphonomethyl)-tyramine.

A composition comprising an N-(phosphonoalkyl)-amino acid, a related compound or derivative of the present invention, preferably an N-(phosphonomethyl)-amino acid, a related compound or derivative thereof is believed to be cosmetically or therapeutically beneficial or effective and can be administered topically or systemically to a mammal, including a human, subject in need of prevention or treatment of cosmetic conditions, dermatological disorders, or diseases associated with the nervous, vascular, musculoskeletal or cutaneous system, or others.

For topical administration, a composition comprising an N-(phosphonoalkyl)-amino acid, a related compound or derivative of the present invention, preferably an N-(phosphonomethyl)-amino acid a related compound or derivative of the present invention, can be topically applied one to three times, and preferably twice, daily to the lesions or the cutaneous sites associated with cosmetic conditions or medical disorders or diseases. The topical application can continue until the symptom, cosmetic condition, medical disorder or disease has been eradicated or substantially improved. The treatment period depends on the condition or severity of the disorder or disease, and also depends on the individual subject. Examples of conditions, disorders and diseases associated with nervous, vascular, musculoskeletal or cutaneous system, or others include, without limitation pains, pruritus, inflammation, erythema, dermatitis, acne, rosacea, eczema, severe dry skin, ichthyosis, age spots, psoriasis, wrinkles, photoaging skin, pigmented skin, and dark skin to be lightened.

As used herein, "percent" or "%" concerning an amount of an ingredient or component means weight percent of the ingredient or component with respect to the overall composition, unless otherwise indicated.

For example, human subjects having severe dry skin or ichthyosis, topically applied 1%-5% N-(phosphonomethyl)-glycine creams to lesions for 2 to 3 weeks. After 2 to 3 weeks of topical application, the thick and scaly skin disappeared and the skin became smooth and normal in appearance. Clinical evaluation was judged to be 90% to 100% improvement compared to the untreated condition or when using a vehicle control.

For systemic administration, a composition comprising an N-(phosphonoalkyl)-amino acid, a related compound or derivative of the present invention, preferably an N-(phosphonomethyl)-amino acid of the present invention, can be administered by injection, infusion or oral intake, or otherwise, with the preferred route being oral administration. A composition comprising an N-(phosphonoalkyl)-amino acid, a related compound or derivative of the present invention, preferably an N-(phosphonomethyl)-amino acid, a related compound or derivative can be taken orally one to three times, and preferably twice, daily for prevention or treatment of disorders and diseases associated with nervous, vascular, musculoskeletal or cutaneous system, or others. The oral administration can continue until the symptom, cosmetic condition, medical disorder or disease has been eradicated or substantially improved. The symptoms or disorders include, without limitation, pains, pruritus, inflammation, erythema, dermatitis, acne, eczema, dementia, Alzheimer's disease, joint pain or swelling, and arthritis. Oral dosages can be about 50 mg to about 500 mg daily, preferably divided into equal dosages of about 25 mg to about 250 mg taken twice daily.

The particularly preferred N-(phosphonomethyl)-amino acids useful in the embodiments described herein, and that can be administered topically or systemically include N-(phosphonomethyl)-asparagine, N-(phosphonomethyl)-asparaginamide, N-(phosphonomethyl)-glycine, N-(phosphonomethyl)-glycinamide, N-(phosphonomethyl)-glycine ethyl ester, N-(phosphonomethyl)-glycine propyl ester, N-(phosphonomethyl)-glycine isopropyl ester, N-(phosphonomethyl)-proline, N-(phosphonomethyl)-prolinamide, N-(phosphonomethyl)-proline ethyl ester, N-(phosphonomethyl)-proline propyl ester, N-(phosphonomethyl)-proline isopropyl ester, N-(phosphonomethyl)-glutamic acid, N-(phosphonomethyl)-glutamic acid diethyl ester, N-(phosphonomethyl)-glutamine, N-(phosphonomethyl)-glutaminamide, N-(phosphonomethyl)-glutamine ethyl ester, N-(phosphonomethyl)-arginine, N-(phosphonomethyl)-argininamide, N-(phosphonomethyl)-arginine ethyl ester, N-(phosphonomethyl)-lysine, N-(phosphonomethyl)-lysinamide, N-(phosphonomethyl)-lysine ethyl ester, N-(phosphonomethyl)-creatine and N-(phosphonomethyl)-creatinine.

In accordance with preferred embodiments of the invention, a composition is provided comprising at least one compound selected from the group consisting of an N-(phosphonoalkyl)-amino acid, a related compound or derivative of the present invention, preferably an N-(phosphonomethyl)-amino acid or derivative thereof, as free acid, ester, amide, lactone or salt form (which includes partial salts) present in a therapeutically or cosmetically effective amount and in a pharmaceutically or cosmetically acceptable vehicle for topical or systemic treatment of disorders associated with nervous, vascular, musculoskeletal or cutaneous system. In one embodiment of the invention, the composition further comprises a cosmetic, pharmaceutical or other topically active agent for synergetic or synergistic effects.

These cosmetic, pharmaceutical or other topically active agent includes any one or more of an agent selected from hydroxyacids, ketoacids and related compounds; phenyl alpha acyloxyalkanoic acids and derivatives; N-acyl-aldosamines, N-acylamino acids and related N-acyl compounds; local analgesics and anesthetics; anti-acne agents; anti-bacterial agents; anti-yeast agents; anti-fungal agents; anti-viral agents; anti-infective agents; anti-dandruff agents; anti-dermatitis agents; anti-eczema agents; anti-histamine agents; anti-pruritic agents; anti-emetics; anti-motion sickness agents; anti-inflammatory agents; anti-hyperkeratotic agents; antiperspirants; anti-psoriatic agents; anti-rosacea agents; anti-seborrheic agents; hair conditioners and hair treatment agents; anti-aging and anti-wrinkle agents; anti-anxiety agents; anti-convulsant agents; anti-depressant agents; sunblock and sunscreen agents; skin lightening agents; depigmenting agents; astringents; cleansing agents; corn, callus or wart removing agents; skin plumping agents; skin volumizing agents; skin firming agents; matrix metalloproteinase (MMP) inhibitors; topical cardiovascular agents; wound-healing agents; gum disease or oral care agents; amino acids; peptides; dipeptides; tripeptides; glutathione and its derivatives; oligopeptides; polypeptides; carbohydrates; aminocarbohydrates; vitamins; corticosteroids; tanning agents; hormones and retinoids.

Non-limiting specific examples of particular cosmetic, pharmaceutical or other topically active agents, as stated or as free base, free acid, ester, amide, lactone or salt form, include for synergetic or synergistic effects: abacavir, abciximab, acamprosate, acarbose, acebutolol, acetaminophen, acetaminosalol, acetazolamide, acetic acid, acetohydroxamic acid, N-acetylcysteine and its esters, N-acetylglutathione and its esters, acitretin, aclometasone dipropionate, acrivastine, acthrel, actidose, actigall, acyclovir, adalimumab, adapalene, adefovir dipivoxil, adenosine, agalsidase, albendazole, albumin, albuterol, aldesleukin, alefacept, alemtuzumab, alendronate, alfuzosin, alitretinoin, allantoin, allium, allopurinol, alloxanthine, almotriptan, alosetron, alpha tocopheral, alpha,-proteinase, alprazolam, alprenolol, alprostadil, alteplase, altretamine, aluminum acetate, aluminum chloride, aluminum chlorohydroxide, aluminum hydroxide, amantadine, amifostine, amiloride, aminacrine, amino acid, aminobenzoate, p-aminobenzoic acid, aminocaproic acid, aminohippurate, aminolevulinic acid, aminosalicylic acid, amiodarone, amitriptyline, amlodipine, amocarzine, amodiaquin, amorolfine, amoxapine, amoxicillin, amphetamine, amphotericin, ampicillin, amprenavir, anagrelide, anakinra, anastrozole, anisindione, anthralin, antihemophilic, antithrombin, anti-thymocyte, antivenin, apomorphine, aprepitant, aprotinin, arbutin, argatroban, aripiprazole, arnica, ascorbic acid and its esters, ascorbyl palmitate, aspirin, atazanavir, atenolol, atomoxetine, atorvastatin, atovaquone, atropine, azathioprine, azelaic acid, azelastine, azithromycin, baclofen, bacitracin, balsalazide, balsam, basiliximab, beclomethasone dipropionate, bemegride, benazepril, bendroflumethiazide, benzocaine, benzonatate, benzophenone, benzoyl peroxide, benztropine, bepridil, beta carotene, betamethasone dipropionate, betamethasone valerate, betaxolol, bethanechol, bevacizumab, bexarotene, bicalutamide, bimatoprost, bioflavonoids, biotin, biperiden, bisacodyl, bisoprolol, bivalirudin, bortezomib, bosentan, botulinum, brimonidine, brinzolamide, bromocriptine, brompheniramine, budesonide, bumetanide, bupivacaine, buprenorphine, bupropion, burimamide, buspirone, busulfan, butabarbital, butalbital, butenafine, butoconazole, butorphanol, butyl aminobenzoate, cabergoline, caffeic acid, caffeine, calcipotriene, calcitonin-salmon, calcitriol, calfactant, camellia sinensis, camphor, candesartan cilexetil, capecitabine, capreomycin, capsaicin, captopril, carbamazepine, carbamide peroxide, carbidopa, carbinoxamine, cefditoren pivoxil, cefepime, cefpodoxime proxetil, celecoxib, cetirizine, cevimeline, chitosan, chlordiazepoxide, chlorhexidine, chloroquine, chlorothiazide, chloroxylenol, chlorpheniramine, chlorpromazine, chlorpropamide, ciclopirox, cilostazol, cimetidine, cinacalcet, ciprofloxacin, citalopram, citric acid, cladribine, clarithromycin, clemastine, clindamycin, clioquinol, clobetasol propionate, clocortolone pivalate, clomiphene, clonidine, clopidogrel, clotrimazole, clozapine, coal tar, coal tar extracts (LCD), codeine, cromolyn, crotamiton, cyclizine, cyclobenzaprine, cycloserine, cytarabine, dacarbazine, dalfopristin, dapsone, daptomycin, daunorubicin, deferoxamine, dehydroepiandrosterone, delavirdine, desipramine, desloratadine, desmopressin, desoximetasone, dexamethasone, dexmedetomidine, dexmethylphenidate, dexrazoxane, dextroamphetamine, diazepam, diclofenac, dicyclomine, didanosine, dihydrocodeine, dihydromorphine, diltiazem, 6,8-dimercaptooctanoic acid (dihydrolipoic acid), diphenhydramine, diphenoxylate, dipyridamole, disopyramide, dobutamine, dofetilide, dolasetron, donepezil, dopa esters, dopamide, dopamine, dorzolamide, doxepin, doxorubicin, doxycycline, doxylamine, doxepin, duloxetine, dyclonine, econazole, efalizumab, eflomithine, eletriptan, emtricitabine, enalapril, ephedrine, epinephrine, epinine, epirubicin, eptifibatide, ergotamine, erythromycin, escitalopram, esmolol, esomeprazole, estazolam, estradiol, etanercept, ethacrynic acid, ethinyl estradiol, etidocaine, etomidate, famciclovir, famotidine, felodipine, fentanyl, ferulic acid, fexofenadine, flecamide, fluconazole, flucytosine, fluocinolone acetonide, fluocinonide, 5-fluorouracil, fluoxetine, fluphenazine, flurazepam, fluticasone propionate, fluvoxamine, formoterol, furosemide, galactarolactone, galactonic acid, galactonolactone, galantamine, gatifloxacin, gefitinib, gemcitabine, gemifloxacin, glucarolactone, gluconic acid, gluconolactone, glucuronic acid, glucuronolactone, glycolic acid, griseofulvin, guaifenesin, guanethidine, N-guanylhistamine, haloperidol, haloprogin, hexylresorcinol, homatropine, homosalate, hydralazine, hydrochlorothiazide, hydrocortisone, hydrocortisone 21-acetate, hydrocortisone 17-butyrate, hydrocortisone 17-valerate, hydrogen peroxide, hydromorphone, hydroquinone, hydroquinone monoether, hydroxyzine, hyoscyamine, hypoxanthine, ibuprofen, ichthammol, idarubicin, imatinib, imipramine, imiquimod, indinavir, indomethacin, infliximab, irbesartan, irinotecan, isoetharine, isoproterenol, itraconazole, kanamycin, ketamine, ketanserin, ketoconazole, ketoprofen, ketotifen, kojic acid, labetalol, lactic acid, lactobionic acid, lamivudine, lamotrigine, lansoprazole, letrozole, leuprolide, levalbuterol, levofloxacin, lidocaine, linezolid, lobeline, loratadine, loperamide, losartan, loxapine, lysergic diethylamide, mafenide, malic acid, maltobionic acid, mandelic acid, maprotiline, mebendazole, mecamylamine, meclizine, meclocycline, memantine, menthol, meperidine, mepivacaine, mequinol, mercaptopurine, mescaline, metanephrine, metaproterenol, metaraminol, metformin, methadone, methamphetamine, methotrexate, methoxamine, methyldopa esters, methyldopamide, 3,4-methylenedioxymethamphetamine, methyllactic acid, methyl nicotinate, methylphenidate, methyl salicylate, metiamide, metolazone, metoprolol, metronidazole, mexiletine, miconazole, midazolam, midodrine, miglustat, minocycline, minoxidil, mirtazapine, mitoxantrone, moexiprilat, molindone, monobenzone, morphine, moxifloxacin, moxonidine, mupirocin, nadolol, naftifine, nalbuphine, nalmefene, naloxone, naproxen, nefazodone, nelfinavir, neomycin, nevirapine, nicardipine, nicotine, nifedipine, nimodipine, nisoldipine, nitrofurantoin, nizatidine, norepinephrine, nystatin, octopamine, octreotide, octyl methoxycinnamate, octyl salicylate, ofloxacin, olanzapine, olmesartan medoxomil, olopatadine, omeprazole, ondansetron, oxiconazole, oxotremorine, oxybenzone, oxybutynin, oxycodone, oxymetazoline, padimate O, palonosetron, pantothenic acid, pantoyl lactone, paroxetine, pemoline, penciclovir, penicillamine, penicillins, pentazocine, pentobarbital, pentostatin, pentoxifylline, pergolide, perindopril, permethrin, phencyclidine, phenelzine, pheniramine, phenmetrazine, phenobarbital, phenol, phenoxybenzamine, phentolamine, phenylephrine, phenylpropanolamine, phenyloin, physostigmine, pilocarpine, pimecrolimus, pimozide, pindolol, pioglitazone, pipamazine, piperonyl butoxide, pirenzepine, podofilox, povidone iodine, pramipexole, pramoxine, prazosin, prednisone, prenalterol, prilocalne, procainamide, procaine, procarbazine, promazine, promethazine, promethazine propionate, propafenone, propoxyphene, propranolol, propylthiouracil, protriptyline, pseudoephedrine, pyrethrin, pyrilamine, pyrimethamine, quetiapine, quinapril, quinethazone, quinidine, quinupristin, rabeprazole, reserpine, resorcinol, retinal, 13-cis retinoic acid, retinoic acid, retinol, retinyl acetate, retinyl palmitate, ribavirin, ribonic acid, ribonolactone, rifampin, rifapentine, rifaximin, riluzole, rimantadine, risedronic acid, risperidone, ritodrine, rivastigmine, rizatriptan, ropinirole, ropivacaine, salicylamide, salicylic acid, salmeterol, scopolamine, selegiline, selenium sulfide, serotonin, sertaconazole, sertindole, sertraline, shale tar, sibutramine, sildenafil, sotalol, streptomycin, strychnine, sulconazole, sulfacetamide, sulfabenz, sulfabenzamide, sulfabromomethazine, sulfacetamide(sodium sulfacetamide), sulfachlorpyridazine, sulfacytine, sulfadiazine, sulfadimethoxine, sulfadoxine, sulfaguanole, sulfalene, sulfamethizole, sulfamethoxazole, sulfanilamide, sulfapyrazine, sulfapyridine, sulfasalazine, sulfasomizole, sulfathiazole, sulfisoxazole, sulfur, tacrolimus, tadalafil, tamsulosin, tartaric acid, tazarotene, tegaserod, telithromycin, telmisartan, temozolomide, tenofovir disoproxil, terazosin, terbinafine, terbutaline, terconazole, terfenadine, tetracaine, tetracycline, tetrahydrozoline, thalidomide, theobromine, theophylline, thiabendazole, thioctic acid (lipoic acid), thioridazine, thiothixene, thymol, tiagabine, timolol, timidazole, tioconazole, tirofiban, tizanidine, tobramycin, tocamide, tolazoline, tolbutamide, tolnaftate, tolterodine, tramadol, tranylcypromine, trazodone, triamcinolone acetonide, triamcinolone diacetate, triamcinolone hexacetonide, triamterene, triazolam, triclosan, triflupromazine, trimethoprim, trimipramine, tripelennamine, triprolidine, tromethamine, tropic acid, tyramine, undecylenic acid, urea, urocanic acid, ursodiol, valacyclovir, vardenafil, venlafaxine, verapamil, vitamin E acetate, voriconazole, warfarin, wood tar, xanthine, zafirlukast, zaleplon, zinc pyrithione, ziprasidone, zolmitriptan and zolpidem.

General Preparations

Compositions of the present invention comprising an N-(phosphonoalkyl)-amino acid, preferably an N-(phosphonomethyl)-amino acid, a related compound or derivative of the present invention can be formulated as an injectable or infusible solution or other formulation or as a topical solution, gel, lotion, cream, ointment, shampoo, spray, stick, pad, powder, masque, mouth rinse or wash, vaginal gel or preparation, or other form acceptable for use on skin, nail, hair, oral mucosa, vaginal or anal mucosa, mouth or gums.

To prepare a solution composition of the present invention, at least one N-(phosphonoalkyl)-amino acid, preferably an N-(phosphonomethyl)-amino acid, a related compound or derivative is dissolved in a solution prepared from water, ethanol, propylene glycol, butylene glycol, and/or other pharmaceutically or cosmetically acceptable vehicle. The concentration of a single N-(phosphonoalkyl)-amino acid, preferably an N-(phosphonomethyl)-amino acid, a related compound or derivative, or the total concentration of all N-(phosphonomethyl)-amino acids where the composition comprises more than one N-(phosphonomethyl)-amino acid, can be about 0.01% to about 99.9%, with a preferred concentration of about 0.1% to about 50%, and a more preferred concentration of about 0.5% to about 10%.

To prepare a topical composition in lotion, cream or ointment form, the N-(phosphonoalkyl)-amino acid, a related compound or derivative of the present invention, preferably an N-(phosphonomethyl)-amino acid, is first dissolved in water, ethanol, propylene glycol, and/or other vehicle, and the solution thus obtained is mixed with a desired base or pharmaceutically or cosmetically acceptable vehicle to make a lotion, cream or ointment. Typical ointments can be made readily with an oil-in-water emulsion, such as hydrophilic ointment U.S.P., as is well known to those skilled in the art in view of the present disclosure. Concentrations of the N-(phosphonoalkyl)-amino acid are the same as described above regarding solutions.

A topical composition of the instant invention can also be formulated in a gel or shampoo form. A typical gel composition is formulated by the addition of a gelling agent such as chitosan, methyl cellulose, ethyl cellulose, polyvinyl alcohol, polyquatemiums, hydroxyethylcellulose, hydroxypropylcellulose, hydroxypropylmethylcellulose, carbomer or ammoniated glycyrrhizinate to a solution comprising the N-(phosphonoalkyl)-amino acid. The preferred concentration of the gelling agent may be about 0.1% to about 4%. In the preparation of shampoo, the N-(phosphonoalkyl)-amino acid, related compound or derivative thereof is first dissolved in water or propylene glycol, and the solution thus obtained is mixed with a shampoo base. Concentrations of the N-(phosphonoalkyl)-amino acid, related compound or derivative thereof used in gel or shampoo form are the same as described above regarding solutions.

To prepare a combination composition for synergetic or synergistic effects, a cosmetic, pharmaceutical or other agent is incorporated into any one of the above compositions by dissolving or mixing the agent into the formulation. Other forms of compositions of the present invention for delivery of the N-(phosphonoalkyl)-amino acid, a related compound or derivative of the present invention, preferably an N-(phosphonomethyl)-amino acid, are readily blended, prepared or formulated by those skilled in the art in view of the present disclosure. For systemic administration the N-(phosphonoalkyl)-amino acid, a related compound or derivative of the present invention, preferably an N-(phosphonomethyl)-amino acid, can be formulated for oral administration or for parenteral injection or infusion. In oral preparations, the N-(phosphonoalkyl)-amino acid can be formulated in tablet form or in gelatin capsules with or without mixing with gelatin powder. Each tablet or capsule can contain about 10 mg to about 300 mg of the N-(phosphonomethyl)-amino acid as free acid, salt, amide, ester or lactone form. For parenteral injection or infusion, the N-(phosphonomethyl)-amino acid is prepared under sterilized conditions, usually in a concentration of about 1% to about 10% in water, propylene glycol and/or non-aqueous vehicle.

The present invention will now be described in more detail with reference to the following non-limiting examples. In the initial tests for comparative studies, a control vehicle was always included. It was discovered that all the vehicle controls gave the same results as that of the untreated skin sites; no detectable effects of the controls have been found as judged by clinical evaluation.

For subjective disorders such as pain, itch or the like, the therapeutic effects were evaluated or judged by the subjects or patients; for example, if the pain or itch had disappeared within hours or days. For other detectable symptoms or syndromes, the therapeutic effects or improvements were evaluated or judged by medical professionals.

EXAMPLE 1

In one of the studies related to skin changes associated with aging, skin thickness was measured by micrometer calipers as follows:

The skin was grasped with a 2×6 cm metal hinge, the internal faces of which were coated with emery cloth to prevent slippage, and manually squeezed to threshold subject discomfort. Combined thickness of two whole-skin layers including thickness of the two hinge leaves was measured with micrometer calipers. Thickness of the two hinge leaves was subtracted to determine the actual thickness of the two whole-skin layers. Triplicate measurements on treated sites were done and an average number was used for calculation of the skin thickness.

EXAMPLE 2

N-(phosphonomethyl)-glycine (5 g) was suspended in water (30 ml) and propylene glycol (10 ml), and concentrated ammonium hydroxide (2 ml) was added with stirring. The suspension became a clear solution, and was mixed with hydrophilic ointment (oil-in-water emulsion, 53 g). The white cream thus formulated had pH 3.8 and contained 5% N-(phosphonomethyl)-glycine. A male subject, age 35, who had X-linked ichthyosis with severe dry skin, having thick and rough skin with adherent scales, topically applied the above 5% N-(phosphonomethyl)-glycine cream to an involved skin site twice daily for two weeks. After one week of topical application, the adherent scales disappeared, and the skin became smooth and had 50% improvement in contrast to the untreated or vehicle control as judged by clinical evaluation. After two weeks of topical application, the treated skin became normal in appearance, and had 100% improvement in contrast to the untreated or vehicle control as judged by clinical evaluation. The above results show that a representative N-(phosphonomethyl)-amino acid would be therapeutically effective for topical treatment of disturbed keratinization and hyperkeratotic conditions including dry skin, severe dry skin, ichthyosis, calluses, keratoses, acne, rosacea, blemished skin, psoriasis and age spots.

EXAMPLE 3

N-(phosphonomethyl)imino-diacetic acid (5 g) was suspended in water (15 ml) and propylene glycol (10 ml), and concentrated ammonium hydroxide (3 ml) was added with stirring. The suspension became a clear solution, and was mixed with hydrophilic ointment (oil-in-water emulsion 67 g). The white cream thus formulated had pH 3.5 and contained 5% N-(phosphonomethyl)imino-diacetic acid.

A male subject, age 35, who had X-linked ichthyosis with severe dry skin, having thick and rough skin with adherent scales, topically applied the above 5% N-(phosphonomethyl) imino-diacetic acid cream to an involved skin site twice daily for two weeks. After one week of topical application, most adherent scales disappeared and the skin had 50% improvement in contrast to the untreated or vehicle control as judged by clinical evaluation. After two weeks of topical application, the scales disappeared completely and the treated skin became smooth, and had 90% improvement in contrast to the untreated or vehicle control as judged by clinical evaluation.

The above results show that another representative N-(phosphonomethyl)-amino acid would be therapeutically effective for topical treatment of disturbed keratinization and hyperkeratotic conditions including dry skin, severe dry skin, ichthyosis, calluses, keratoses, acne, rosacea, blemished skin, psoriasis and age spots.

EXAMPLE 4

N-(phosphonomethyl)-glycine ethyl ester (5 g) was dissolved in warm water (20 ml) and propylene glycol (20 ml), and the solution thus obtained was mixed with hydrophilic ointment (oil-in-water emulsion, 55 g). The white cream thus formulated had pH 1.2 and contained 5% N-(phosphonomethyl)-glycine ethyl ester.

A male subject, age 86, had chronic plaque psoriasis with erythema, moderately thick and silvery scales. The subject topically applied twice daily the above white cream containing 5% N-(phosphonomethyl)-glycine ethyl ester to one psoriatic lesion for two weeks. At the end of two weeks, the erythema and silvery scales improved substantially, and the treated skin had 50% improvement in contrast to the untreated or vehicle control as judged by clinical evaluation.

EXAMPLE 5

N-(phosphonomethyl)-L-tyrosine (5 g) was dissolved in warm propylene glycol (40 ml), and the solution thus obtained was mixed with hydrophilic ointment (oil-in-water emulsion, 55 g). The white cream thus formulated had pH 2.3 and contained 5% N-(phosphonomethyl)-L-tyrosine.

A male subject, age 35, who had X-linked ichthyosis with severe dry skin, having thick and rough skin with adherent scales, topically applied the above 5% N-(phosphonomethyl)-L-tyrosine cream to an involved skin site twice daily for 12 days. After 12 days of topical application, most adherent scales disappeared and the skin became smooth, and had 75% improvement in contrast to the untreated or vehicle control as judged by clinical evaluation.

The above results show that another representative N-(phosphonomethyl)-amino acid would be therapeutically effective for topical treatment of disturbed keratinization and hyperkeratotic conditions including dry skin, severe dry skin, ichthyosis, calluses, keratoses, acne, rosacea, blemished skin, psoriasis and age spots.

EXAMPLE 6

N-(phosphonomethyl)-L-proline (5 g) was suspended in water (20 ml), and concentrated ammonium hydroxide (0.8 ml) was added. The solution thus obtained was mixed with hydrophilic ointment (oil-in-water emulsion, 74.2 g). The white cream thus formulated had pH 3.2 and contained 5% N-(phosphonomethyl)-L-proline. Under the same procedure, a white cream containing 10% N-(phosphonomethyl)-L-proline was formulated from N-(phosphonomethyl)-L-proline (10 g), water (20 ml), concentrated ammonium hydroxide (1 ml), and hydrophilic ointment (oil-in-water emulsion, 69 g).

A male subject, age 86, had chronic plaque psoriasis with erythema, moderately thick and silvery scales. The subject topically applied twice daily the above white cream containing 10% N-(phosphonomethyl)-L-proline to one psoriatic lesion for two weeks. At the end of two weeks, the erythema and silvery scales improved very substantially, and the treated skin had 75% improvement in contrast to the untreated or vehicle control as judged by clinical evaluation.

The above results show that yet another representative N-(phosphonomethyl)-amino acid would be therapeutically effective for topical treatment of disturbed keratinization and inflammatory conditions including erythema, eczema, dermatitis, dermatoses, itch, psoriasis, acne and rosacea.

EXAMPLE 7

N-(phosphonomethyl)-DL-asparagine (6 g) was dissolved in warm water (30 ml) and propylene glycol (10 ml), and the solution thus obtained was mixed with hydrophilic ointment (oil-in-water emulsion, 54 g). The white cream thus formulated had pH 2.2 and contained 6% N-(phosphonomethyl)-DL-asparagine.

N-(phosphonomethyl)-DL-asparagine (5 g) was dissolved in warm water (30 ml) and propylene glycol (10 ml), and the solution thus obtained was mixed with hydrophilic ointment (oil-in-water emulsion, 55 g). The white cream thus formulated had pH 2.2 and contained 5% N-(phosphonomethyl)-DL-asparagine.

A male subject, age 36, who had X-linked ichthyosis having thick and rough skin with adherent scales, topically applied the 5% N-(phosphonomethyl)-DL-asparagine cream to an involved skin site twice daily for three weeks. After one week of topical application, most adherent scales disappeared and the treated site appeared smooth. The skin had 75% improvement in contrast to the untreated or vehicle control as judged by clinical evaluation. After three weeks of topical application, the scales disappeared completely and the treated site felt smooth and normal in appearance. The skin had 100% improvement in contrast to the untreated or vehicle control as judged by clinical evaluation.

The above results show that another N-(phosphonomethyl)-amino acid would be therapeutically effective for topical treatment of disturbed keratinization and hyperkeratotic conditions including dry skin, severe dry skin, ichthyosis, calluses, keratoses, acne, rosacea, blemished skin, psoriasis and age spots.

EXAMPLE 8

A male subject, age 36, who had hyperpigmented dark skin, topically applied 5% N-(phosphonomethyl)-DL-asparagine cream prepared according to Example 7 to an involved skin site twice daily for four weeks. After two weeks of topical application, the treated site had mild depigmentation and showed lighter skin color as compared to untreated skin site. The treated site was 25% lighter in skin color in contrast to the untreated or vehicle control as judged by clinical evaluation. After four weeks of topical application, the treated site had substantial reduction in skin pigmentation. The treated site was 50% lighter in contrast to the untreated or vehicle control in skin color as judged by clinical evaluation.

The above results show that a representative N-(phosphonomethyl)-amino acid would be effective for topical treatment of hyperpigmented skin, age spots, melasma, lentigines, mottled skin, aging related skin changes, and would be topically effective for skin lightening.

EXAMPLE 9

N-(phosphonomethyl)-glycine propyl ester (10 g) was dissolved in warm water (20 ml), propylene glycol (10 ml) and 2-amino-2-methyl-1-propanol (5 ml). The clear solution thus obtained was mixed with hydrophilic ointment (oil-in-water emulsion, 55 g). The white cream thus formulated had pH 5.1, and contained 10% N-(phosphonomethyl)-glycine propyl ester. Under the same procedure, a white cream containing 5% N-(phosphonomethyl)-glycine propyl ester was formulated from N-(phosphonomethyl)-glycine propyl ester (5 g), warm water (20 ml), propylene glycol (10 ml), 2-amino-2-methyl-1-propanol (2.5 ml) and hydrophilic ointment (oil-in-water emulsion, 62.5 g).

A male subject, age 86, had chronic plaque psoriasis with erythema, moderately thick and silvery scales. The subject topically applied twice daily the above white cream containing 5% N-(phosphonomethyl)-glycine propyl ester to one psoriatic lesion for two weeks. At the end of two weeks, the erythema and silvery scales improved very substantially, and the treated skin had 75% improvement in contrast to the untreated or vehicle control as judged by clinical evaluation.

The above results show that still another representative N-(phosphonomethyl)-amino acid derivative would be therapeutically effective for topical treatment of disturbed keratinization and inflammatory conditions including erythema, eczema, dermatitis, dermatoses, itch, psoriasis, acne and rosacea.

EXAMPLE 10

N-(phosphonomethyl)-glycine isopropyl ester (10 g) was dissolved in water (10 ml), propylene glycol (20 ml) and meglumine (N-methyl-D-glucamine, 4 g). The solution thus obtained was mixed with hydrophilic ointment (oil-in-water emulsion, 56 g). The white cream thus formulated had pH 1.1, and contained 10% N-(phosphonomethyl)-glycine isopropyl ester. Under the same procedure, a white cream containing 5% N-(phosphonomethyl)-glycine isopropyl ester was formulated from N-(phosphonomethyl)-glycine isopropyl ester (5 g), water (10 ml), propylene glycol (20 ml), meglumine (2 g) and hydrophilic ointment (63 g).

A male subject, age 86, had chronic plaque psoriasis with erythema, moderately thick and silvery scales. The subject topically applied twice daily the above white cream containing 5% N-(phosphonomethyl)-glycine isopropyl ester to one psoriatic lesion for a week. At the end of one week, the erythema and silvery scales improved substantially, and the treated skin had 50% improvement in contrast to the untreated or vehicle control as judged by clinical evaluation.

EXAMPLE 11

N-(phosphonomethyl)-glycinamide (5 g) was dissolved in water (10 ml) and propylene glycol (30 ml), and the mixture thus obtained was mixed with hydrophilic ointment (oil-in-water emulsion, 55 g). The white cream thus formulated had pH 2.1 and contained 5% N-(phosphonomethyl)-glycinamide. Under the same procedure, a white cream containing 8% N-(phosphonomethyl)-glycinamide was formulated from N-(phosphonomethyl)-glycinamide (8 g), water (10 ml), propylene glycol (30 ml) and hydrophilic ointment (52 g).

A male subject, age 86, had chronic plaque psoriasis with erythema, moderately thick and silvery scales. The subject topically applied twice daily the above white cream containing 8% N-(phosphonomethyl)-glycinamide to one psoriatic lesion for three weeks. At the end of three weeks, the erythema and silvery scales disappeared almost completely, and the treated skin had 90% improvement in contrast to the untreated or vehicle control as judged by clinical evaluation.

The above results show that another representative N-(phosphonomethyl)-amino acid derivative would be therapeutically effective for topical treatment of disturbed keratinization and inflammatory conditions including erythema, eczema, dermatitis, dermatoses, itch, psoriasis, acne and rosacea.

EXAMPLE 12

N-(phosphonomethyl)-L-tyrosine ethyl ester (5 g) was dissolved in warm propylene glycol (20 ml) and water (10 ml). The solution thus obtained was mixed with hydrophilic ointment (oil-in-water emulsion, 65 g). The white cream thus formulated had pH 1.2 and contained 5% N-(phosphonomethyl)-L-tyrosine ethyl ester.

A male subject, age 36, who had X-linked ichthyosis having thick and rough skin with adherent scales, topically applied the above 5% N-(phosphonomethyl)-L-tyrosine ethyl ester cream to an involved skin site twice daily for one week. After one week of topical application, most adherent scales disappeared and the treated skin had 25% improvement in contrast to the untreated or vehicle control as judged by clinical evaluation.

The above results show that another N-(phosphonomethyl)-amino acid would be therapeutically effective for topical treatment of disturbed keratinization and hyperkeratotic conditions including dry skin, severe dry skin, ichthyosis, calluses, keratoses, acne, rosacea, blemished skin, psoriasis and age spots.

A male subject, age 86, had chronic plaque psoriasis with erythema, moderately thick and silvery scales. The subject topically applied twice daily the above white cream containing 5% N-(phosphonomethyl)-L-tyrosine ethyl ester to one psoriatic lesion for two weeks. At the end of two weeks, the erythema and silvery scales improved noticeably and the treated skin had 25% improvement in contrast to the untreated or vehicle control as judged by clinical evaluation.

The above results show that another representative N-(phosphonomethyl)-amino acid derivative would be therapeutically effective for topical treatment of disturbed keratinization and inflammatory conditions including erythema, eczema, dermatitis, dermatoses, itch, psoriasis, acne and rosacea.

EXAMPLE 13

N-(phosphonomethyl)-D-4-hydroxyphenylglycine (5 g) was dissolved in water (10 ml) and propylene glycol (20 ml), and the mixture thus obtained was mixed with hydrophilic ointment (oil-in-water emulsion, 65 g). The white cream thus formulated had pH 2.4, and contained 5% N-(phosphonomethyl)-D-4-hydroxyphenylglycine. Under the same procedure, a white cream containing 10% N-(phosphonomethyl)-D-4-hydroxyphenylglycine was formulated from N-(phosphonomethyl)-D-4-hydroxyphenylglycine (10 g), water (10 ml), propylene glycol (20 ml), and hydrophilic ointment (60 g).

A male subject, age 86, had chronic plaque psoriasis with erythema, moderately thick and silvery scales. The subject topically applied twice daily the above white cream containing 10% N-(phosphonomethyl)-D-4-hydroxyphenylglycine to one psoriatic lesion for two weeks. At the end of two weeks, the erythema and silvery scales improved very substantially, and the treated skin had 70% improvement in contrast to the untreated or vehicle control as judged by clinical evaluation.

EXAMPLE 14

N-(phosphonomethyl)-L-serine (6 g) was dissolved in warm propylene glycol (10 ml) and water (30 ml). The solution thus obtained was mixed with hydrophilic ointment (oil-in-water emulsion, 54 g). The white cream thus formulated had pH 1.7 and contained 6% N-(phosphonomethyl)-L-serine.

EXAMPLE 15

N-(phosphonomethyl)-L-proline ethyl ester (8 g) was dissolved in water (10 ml), propylene glycol (20 ml) and ethylenediamine (4 ml). The solution thus obtained was mixed with hydrophilic ointment (oil-in-water emulsion, 58 g). The white cream thus formulated had pH 5.9, and contained 8% N-(phosphonomethyl)-L-proline ethyl ester.

A male subject, age 74, having itchy eczema on his right thigh, topically applied the above 8% N-(phosphonomethyl)-L-proline ethyl ester cream. The itch disappeared within a few minutes after the topical application. The treated skin did not itch for the next 8 hours. Therapeutic evaluation was judged to be 100% effective in contrast to the untreated or vehicle control for immediate relief of itch.

The above result shows that a representative N-(phosphonomethyl)-amino acid derivative would be therapeutically effective for topical treatment of disturbed keratinization and inflammatory conditions including erythema, eczema, dermatitis, dermatoses, itch, psoriasis, acne and rosacea.

EXAMPLE 16

N-(phosphonomethyl)-L-serine ethyl ester (6 g) was dissolved in warm propylene glycol (30 ml). The solution thus obtained was mixed with hydrophilic ointment (oil-in-water emulsion, 64 g). The white cream thus formulated had pH 1.3 and contained 6% N-(phosphonomethyl)-L-serine ethyl ester.

EXAMPLE 17

N-(phosphonomethyl)-creatine (7 g) was dissolved in water (30 ml) and propylene glycol (10 ml), and the solution thus obtained was mixed with hydrophilic ointment (oil-in-water emulsion, 53 g). The white cream thus formulated had pH 1.8 and contained 7% N-(phosphonomethyl)-creatine. Under the same procedure, a white cream containing 5% N-(phosphonomethyl)-creatine was formulated from N-(phosphonomethyl)-creatine (5 g), water (30 ml), propylene glycol (10 ml), and hydrophilic ointment or oil-in-water emulsion (55 g). Under the same procedure, a white cream containing 10% N-(phosphonomethyl)-creatine was formulated from N-(phosphonomethyl)-creatine (10 g), water (30 ml), propylene glycol (10 ml), and hydrophilic ointment (oil-in-water emulsion, 50 g).

A male subject, age 86, had chronic plaque psoriasis with erythema, moderately thick and silvery scales. The subject topically applied twice daily the above white cream containing 5% N-(phosphonomethyl)-creatine to one psoriatic lesion for two weeks. At the end of two weeks, the erythema and silvery scales improved substantially, and the treated skin had 50% improvement in contrast to the untreated or vehicle control as judged by clinical evaluation.

EXAMPLE 18

A male subject, age 74, having itchy eczema on his left leg, topically applied 7% N-(phosphonomethyl)-creatine cream prepared according to Example 17. The itch disappeared within a few minutes after the topical application. The treated skin did not itch for the next 8 hours. Therapeutic evaluation was judged to be 100% effective in contrast to the untreated or vehicle control for immediate relief of itch.

The above results show that a representative N-(phosphonomethyl)-amino acid would be therapeutically effective for topical treatment of disturbed keratinization and inflammatory conditions including erythema, eczema, dermatitis, dermatoses, itch, psoriasis, acne and rosacea.

EXAMPLE 19

N-(phosphonomethyl)-creatine (2 g) was dissolved in (98 ml) of a solution prepared from water (40 parts by volume), ethanol (40 parts by volume) and propylene glycol (20 parts by volume). The composition thus prepared had pH 2.5 and contained 2% N-(phosphonomethyl)-creatine in solution.

N-(phosphonomethyl)-creatine (5 g) was dissolved in (95 ml) solution prepared from water (40 parts by volume), ethanol (40 parts by volume) and propylene glycol (20 parts by volume). The composition thus prepared contained 5% N-(phosphonomethyl)-creatine in solution.

A male subject, age 35, who had X-linked ichthyosis having thick and rough skin with adherent scales, topically applied the above 5% N-(phosphonomethyl)-creatine solution to an involved skin site once every other with occlusion for two weeks. After 10 days of topical application, most adherent scales disappeared and the skin had 50% improvement in contrast to the untreated or vehicle control as judged by clinical evaluation. After two weeks of topical application, the scales disappeared completely and the treated skin became normal in appearance, and had 100% improvement in contrast to the untreated or vehicle control as judged by clinical evaluation.

The above results show that another representative N-(phosphonomethyl)-amino acid would be therapeutically effective for topical treatment of disturbed keratinization and hyperkeratotic conditions including dry skin, severe dry skin, ichthyosis, calluses, keratoses, acne, rosacea, blemished skin, psoriasis and age spots.

EXAMPLE 20

N-(phosphonomethyl)-tyramine (5 g) was suspended in warm propylene glycol (30 ml), and water (5 ml), and the mixture thus obtained was mixed with hydrophilic ointment (oil-in-water emulsion, 60 g). The white cream thus formulated had pH 2.1 and contained 5% N-(phosphonomethyl)-tyramine.

A male subject, age 86, had chronic plaque psoriasis with erythema, moderately thick and silvery scales. The subject topically applied twice daily the above white cream containing 5% N-(phosphonomethyl)-tyramine to one psoriatic lesion for two weeks. At the end of two weeks, the erythema and silvery scales improved substantially, and the treated skin had 50% improvement in contrast to the untreated or vehicle control as judged by clinical evaluation.

EXAMPLE 21

N-(phosphonomethyl)-DL-asparagine (5 g) was dissolved in (95 ml) of a solution prepared from water (40 parts by volume), ethanol (40 parts by volume) and propylene glycol (20 parts by volume). The composition thus prepared had 2.7, and contained 5% N-(phosphonomethyl)-DL-asparagine in solution.

A male subject, age 36, who had hyperpigmented dark skin, topically applied the above 5% N-(phosphonomethyl)-DL-asparagine solution to an involved skin site once every other day with occlusion for ten days. After seven days of topical application, the treated site had mild depigmentation and showed lighter skin color as compared to untreated skin site. The treated site was 25% lighter in skin color as judged by clinical evaluation. After ten days of topical application, the treated site had substantial reduction in skin pigmentation. The treated site was 50% lighter in skin color in contrast to the untreated or vehicle control as judged by clinical evaluation.

The above results show that a representative N-(phosphonomethyl)-amino acid would be effective for topical treatment of hyperpigmented skin, age spots, melasma, lentigines, mottled skin, aging related skin changes, and would be topically effective for skin lightening.

EXAMPLE 22

A male subject, age 36, who had X-linked ichthyosis having thick and rough skin with adherent scales, topically applied the 5% N-(phosphonomethyl)-DL-asparagine solution prepared according to Example 21 to an involved skin site once every other day under occlusion for three weeks. After one week of topical application, most adherent scales disappeared and the treated site appeared smooth. The skin had 75% improvement in contrast to the untreated or vehicle control as judged by clinical evaluation. After three weeks of topical application, the treated skin site appeared normal, and the skin had 100% improvement in contrast to the untreated or vehicle control as judged by clinical evaluation.

The above results show that a representative N-(phosphonomethyl)-amino acid would be therapeutically effective for topical treatment of disturbed keratinization and hyperkeratotic conditions including dry skin, severe dry skin, ichthyosis, calluses, keratoses, acne, rosacea, blemished skin, psoriasis and age spots.

EXAMPLE 23

N-(phosphonomethyl)-creatine (5 g) was dissolved in (95 ml) solution prepared from water (40 parts by volume), ethanol (40 parts by volume) and propylene glycol (20 parts by volume). The composition thus prepared had pH 2.5, and contained 5% N-(phosphonomethyl)-creatine in solution.

A male subject, age 36, who had hyperpigmented dark skin, topically applied the above 5% N-(phosphonomethyl)-creatine solution to an involved skin site once every other day with occlusion for two weeks. After seven days of topical application, the treated site had mild depigmentation and showed lighter skin color as compared to untreated skin site. The treated site was 25% lighter in skin color in contrast to the untreated or vehicle control as judged by clinical evaluation. After two weeks of topical application, the treated site had very substantial reduction in skin pigmentation. The treated site was 75% lighter in skin color in contrast to the untreated or vehicle control as judged by clinical evaluation.

The above results show that a representative N-(phosphonomethyl)-amino acid would be effective for topical treatment of hyperpigmented skin, age spots, melasma, lentigines, mottled skin, aging related skin changes, and would be topically effective for skin lightening.

EXAMPLE 24

N-(phosphonomethyl)-glycinamide (5 g) was dissolved in (95 ml) of a solution prepared from water (40 parts by volume), ethanol (40 parts by volume) and propylene glycol (20 parts by volume). The composition thus prepared had pH 2.5, and contained 5% N-(phosphonomethyl)-glycinamide in solution.

A male subject, age 36, who had hyperpigmented dark skin, topically applied the above 5% N-(phosphonomethyl)-glycinamide solution to an involved skin site once every other day with occlusion for two weeks. After seven days of topical application, the treated site had mild depigmentation and showed lighter skin color as compared to untreated skin site. The treated site was 25% lighter in skin color in contrast to the untreated or vehicle control as judged by clinical evaluation. After two weeks of topical application, the treated site had substantial reduction in skin pigmentation. The treated site was 50% lighter in skin color in contrast to the untreated or vehicle control as judged by clinical evaluation.

The above results show that another representative N-(phosphonomethyl)-amino acid derivative would be effective for topical treatment of hyperpigmented skin, age spots, melasma, lentigines, mottled skin, aging related skin changes, and would be topically effective for skin lightening.

EXAMPLE 25

A male subject, age 36, who had X-linked ichthyosis having thick and rough skin with adherent scales, topically applied 5% N-(phosphonomethyl)-glycinamide solution prepared according to Example 24 to an involved skin site once every other day for three weeks. After one week of topical application, most adherent scales disappeared and the treated site appeared smooth. The skin had 75% improvement in contrast to the untreated or vehicle control as judged by clinical evaluation. After three weeks of topical application, the treated skin site appeared normal, and the skin had 100% improvement in contrast to the untreated or vehicle control as judged by clinical evaluation.

The above results show that another N-(phosphonomethyl)-amino acid derivative would be therapeutically effective for topical treatment of disturbed keratinization and hyperkeratotic conditions including dry skin, severe dry skin, ichthyosis, calluses, keratoses, acne, rosacea, blemished skin, psoriasis and age spots.

EXAMPLE 26

N-(phosphonomethyl)-L-glutamine (5 g) was dissolved in (95 ml) of a solution prepared from water (40 parts by volume), ethanol (40 parts by volume) and propylene glycol (20 parts by volume). The composition thus prepared had pH 2.0, and contained 5% N-(phosphonomethyl)-L-glutamine in solution.

A male subject, age 36, who had hyperpigmented dark skin, topically applied the above 5% N-(phosphonomethyl)-L-glutamine solution to an involved skin site once every other day with occlusion for two weeks. After two weeks of topical application, the treated site had substantial reduction in skin pigmentation. The treated site had 50% lighter in skin color in contrast to the untreated or vehicle control as judged by clinical evaluation.

The above result shows that another representative N-(phosphonomethyl)-amino acid would be effective for topical treatment of hyperpigmented skin, age spots, melasma, lentigines, mottled skin, aging related skin changes, and would be topically effective for skin lightening.

EXAMPLE 27

A male subject, age 36, who had X-linked ichthyosis having thick and rough skin with adherent scales, topically applied 5% N-(phosphonomethyl)-L-glutamine solution prepared according to Example 26 to an involved skin site once every other day for three weeks. After two weeks of topical application, most scales disappeared and the treated site felt nearly smooth, and the skin had 75% improvement in contrast to the untreated or vehicle control as judged by clinical evaluation. After three weeks of topical application, the treated site appeared normal, and the skin had 100% improvement in contrast to the untreated or vehicle control as judged by clinical evaluation.

The above results show that another representative N-(phosphonomethyl)-amino acid would be therapeutically effective for topical treatment of disturbed keratinization and hyperkeratotic conditions including dry skin, severe dry skin, ichthyosis, calluses, keratoses, acne, rosacea, blemished skin, psoriasis and age spots.

EXAMPLE 28

N-(phosphonomethyl)-tyramine (5 g) and concentrated ammonium hydroxide solution (1 ml) were dissolved in a solution (94 ml) prepared from water (40 parts by volume), ethanol (40 parts by volume) and propylene glycol (20 parts by volume). The composition thus prepared had pH 7.1 and contained 5% N-(phosphonomethyl)-tyramine in solution.

A male subject, age 36, who had X-linked ichthyosis having thick and rough skin with adherent scales, topically applied the above 5% N-(phosphonomethyl)-tyramine solution to an involved skin site once every other day under occlusion for a week. After one week of topical application, most adherent scales disappeared and the treated site appeared smooth. The skin had 75% improvement in contrast to the untreated or vehicle control as judged by clinical evaluation.

The above results show that another representative N-(phosphonomethyl)-amino acid would be therapeutically effective for topical treatment of disturbed keratinization and hyperkeratotic conditions including dry skin, severe dry skin, ichthyosis, calluses, keratoses, acne, rosacea, blemished skin, psoriasis and age spots.

EXAMPLE 29

N-(phosphonomethyl)-glutamine (3 g) was dissolved in (97 ml) of a solution prepared from water (80 parts by volume) and propylene glycol (20 parts by volume). The composition thus prepared had pH 2.0 and contained 3% N-(phosphonomethyl)-L-glutamine in solution.

N-(phosphonomethyl)-L-glutamine (10 g) was dissolved in warm water (20 ml) and propylene glycol (10 ml), and the solution thus obtained was mixed with hydrophilic ointment (oil-in-water emulsion, 60 g). The white cream thus formulated had pH 1.3 and contained 10% N-(phosphonomethyl)-L-glutamine.

A male subject, age 74, having itchy eczema on his left thigh, topically applied the above 10% N-(phosphonomethyl)-glutamine. The itch disappeared within a few minutes after the topical application. The treated skin did not itch for the next 8 hours. Therapeutic evaluation was judged to be 100% effective in contrast to the untreated or vehicle control for immediate relief of itch.

The above results show that a representative N-(phosphonomethyl)-amino acid would be therapeutically effective for topical treatment of disturbed keratinization and inflammatory conditions including erythema, eczema, dermatitis, dermatoses, itch, psoriasis, acne and rosacea.

EXAMPLE 30

N-(phosphonomethyl)-L-glutamine (6 g) was dissolved in warm water (40 ml), and the solution thus obtained was mixed with hydrophilic ointment (oil-in-water emulsion, 54 g). The white cream thus formulated had pH 1.5 and contained 6% N-(phosphonomethyl)-L-glutamine.

EXAMPLE 31

N-(phosphonomethyl)-L-glutamic acid (8 g) was dissolved in water (20 ml) and propylene glycol (10 ml), and the solution thus obtained was mixed with hydrophilic ointment (oil-in-water emulsion, 62 g). The white cream thus formulated had pH 2.4 and contained 8% N-(phosphonomethyl)-L-glutamic acid.

A male subject, age 86, had chronic plaque psoriasis with erythema, moderately thick and silvery scales. The subject topically applied twice daily the above white cream containing 8% N-(phosphonomethyl)-L-glutamic acid to one psoriatic lesion for two weeks. At the end of two weeks, the erythema and silvery scales improved substantially and the treated skin had 50% improvement in contrast to the untreated or vehicle control as judged by clinical evaluation.

The above results show that another representative N-(phosphonomethyl)-amino acid derivative would be therapeutically effective for topical treatment of disturbed keratinization and inflammatory conditions including erythema, eczema, dermatitis, dermatoses, itch, psoriasis, acne and rosacea.

EXAMPLE 32

N-(phosphonomethyl)-γ-aminobutanoic acid (10 g) was dissolved in water (20 ml) and propylene glycol (10 ml), and the solution thus obtained was mixed with hydrophilic ointment (oil-in-water emulsion, 60 g). The white cream thus formulated had pH 1.9 and contained 10% N-(phosphonomethyl)-γ-aminobutanoic acid.

EXAMPLE 33

N-(phosphonomethyl)-L-glutathione (5 g) was dissolved in (95 ml) of a warm solution prepared from water (40 parts by volume), ethanol (40 parts by volume) and propylene glycol (20 parts by volume). The composition thus prepared had pH 2.3 and contained 5% N-(phosphonomethyl)-L-glutathione in solution.

EXAMPLE 34

N-(phosphonomethyl)-L-cysteine (5 g) was dissolved in (95 ml) of a warm solution prepared from water (40 parts by volume), ethanol (40 parts by volume) and propylene glycol (20 parts by volume). The composition thus prepared had pH 2.7 and contained 5% N-(phosphonomethyl)-L-cysteine in solution.

EXAMPLE 35

N-(phosphonomethyl)-guanidinoacetic acid [N-(phosphonomethyl)-glycocyamine, 1 g] was dissolved in a solution (99 ml) prepared from water (80 parts by volume) and propylene glycol (20 parts by volume). The composition thus prepared had pH 2.1, and contained 1% N-(phosphonomethyl)-guanidinoacetic acid in solution.

EXAMPLE 36

The following is a typical process for preparing a composition comprising an N-(phosphonomethyl)-amino acid or derivative for oral administration.

N-(Phosphonomethyl)-glycine crystals were converted to fine powder by grinding with mortar and pestle. Lilly® gelatin capsules size No. 1, were filled to the top with N-(phosphonomethyl)-glycine powder without mixing with gelatin powder. Each capsule thus prepared contained 300 mg N-(phosphonomethyl)-glycine.

A subject can take orally one or two capsules per day for systemic administration to alleviate or improve cosmetic conditions, or medical disorders, symptoms or syndromes associated with the nervous, vascular, musculoskeletal or cutaneous system, or others.

EXAMPLE 37

N-(Phosphonomethyl)-L-tyrosine crystals were converted to fine powder by grinding with mortar and pestle. Lilly® gelatin capsules size No. 1, were filled to the top with N-(phosphonomethyl)-L-tyrosine powder without mixing with gelatin powder. Each capsule thus prepared contained 120 mg N-(phosphonomethyl)-L-tyrosine.

A subject can take orally one or two capsules per day for systemic administration to alleviate or improve cosmetic conditions, or medical disorders, symptoms or syndromes associated with the nervous, vascular, musculoskeletal or cutaneous system, or others.

EXAMPLE 38

N-(Phosphonomethyl)-L-serine crystals were converted to fine powder by grinding with mortar and pestle. Lilly® gelatin capsules size No. 1, were filled to the top with N-(phosphonomethyl)-L-serine powder without mixing with gelatin powder. Each capsule thus prepared contained 130 mg N-(phosphonomethyl)-L-serine.

A subject can take orally one or two capsules per day for systemic administration to alleviate or improve cosmetic conditions, or medical disorders, symptoms or syndromes associated with the nervous, vascular, musculoskeletal or cutaneous system, or others.

EXAMPLE 39

N-(Phosphonomethyl)-L-proline crystals were converted to fine powder by grinding with mortar and pestle. Lilly® gelatin capsules size No. 1, were filled to the top with N-(phosphonomethyl)-L-proline powder without mixing with gelatin powder. Each capsule thus prepared contained 150 mg N-(phosphonomethyl)-L-proline.

A subject can take orally one or two capsules per day for systemic administration to alleviate or improve cosmetic conditions, or medical disorders, symptoms or syndromes associated with the nervous, vascular, musculoskeletal or cutaneous system, or others.

EXAMPLE 40

N-(Phosphonomethyl)-creatinine (5 g) was dissolved in 95 ml of a solution prepared from water (80 parts by volume) and propylene glycol (20 parts by volume). The liquid composition thus prepared had pH 4.8 and contained 5% N-(phosphonomethyl)-creatinine. This composition would be topically effective for treatment or prevention of cosmetic conditions or medical disorders, symptoms or syndromes associated with nervous, vascular, musculoskeletal or cutaneous system, or others.

EXAMPLE 41

N-(Phosphonomethyl)-L-ornithine (8 g) was dissolved in 92 ml of a solution prepared from water (80 parts by volume) and propylene glycol (20 parts by volume). The liquid composition thus prepared had pH 1.4 and contained 8% N-(phosphonomethyl)-L-ornithine. This composition would be topically effective for treatment or prevention of cosmetic conditions or medical disorders, symptoms or syndromes associated with nervous, vascular, musculoskeletal or cutaneous system, or others.

EXAMPLE 42

N,N-Bis(phosphonomethyl)-glycine (2.5 g) was dissolved in water (10 ml), and the solution thus obtained was mixed with hydrophilic ointment (oil-in-water emulsion, 87.5 g). The white cream thus formulated had pH 1.3 and contained 2.5% N,N-bis(phosphonomethyl)-glycine.

EXAMPLE 43

N-(phosphonomethyl)-4-guanidinobutanoic acid (5 g) was dissolved in water (20 ml), and the solution thus obtained was mixed with hydrophilic ointment (oil-in-water emulsion, 75 g). The white cream thus formulated had pH 1.8 and contained 5% N-(phosphonomethyl)-4-guanidinobutanoic acid.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:
1. A composition comprising an N-(phosphonoalkyl)-amino acid, a related compound or a derivative thereof in a form as a free acid, salt, partial salt, lactone, amide or ester, or in stereoisomeric or non-stereoisomeric form, and a cosmetically or pharmaceutically acceptable vehicle for topical or systemic administration to a mammalian subject for treatment of a cosmetic condition or dermatological disorder;
wherein the N-(phosphonoalkyl)-amino acid, related compound or derivative thereof is N-(phosphonoalkyl)-proline or has the following formula:

$R_1CH(NR_2R_3)(CH_2)_mCOR_4$ wherein $R_1$ is H, and alkyl group having 1 to 19 carbon atoms, an aryl group having 6 to 19 carbon atoms or an aralkyl group having 7 to 19 carbon atoms; and $R_1$ can also carry —OH, —SH, —SCH$_3$, —NH$_2$, —NR$_2$R$_3$, —COR$_4$, —NHCONH$_2$, —NHC(=NR$_2$)NH$_2$, imidazole, pyrrolidine or other heterocyclic group; m is an integer from 0 to 5; $R_2$ is a phosphonoalkyl group having a formula (HO)$_2$PO(CH$_2$)$_n$—; $R_3$ is H or a phosphonoalkyl group having a formula (HO)$_2$PO(CH$_2$)$_n$—; n is an integer from 1 to 9; $R_4$ is —NH$_2$ or —OR$_5$, $R_5$ is H, and alkyl group having 1 to 19 carbon atoms, an aryl group having 6 to 19 carbon atoms or an aralkyl group having 7 to 19 carbon atoms; and the H attached to any carbon atom can be substituted by I, F, Cl, Br, OH or an alkoxy group having 1 to 9 carbon atoms; and
wherein the N-(phosphonoalkyl)-amino acid, related compound or derivative thereof is in a form as a free acid, salt, partial salt, lactone, amide or ester, or in stereoisomeric or non-stereoisomeric form.

2. The composition of claim 1, wherein the related compound or derivative is an N,N-bis(phosphonoalkyl)-amino acid or an N,N'-bis(phosphonoalkyl)-amino acid.

3. The composition of claim 2, wherein the related compound or derivative is an N,N-bis(phosphonomethyl)-amino acid or an N,N'-bis(phosphonomethyl)-amino acid.

4. The composition of claim 3, wherein the N,N-bis(phosphonomethyl)-amino acid or N,N'-bis(phosphonomethyl)-amino acid in a form as a free acid, salt, partial salt, lactone, amide or ester, or in stereoisomeric or non-stereoisomeric form, is selected from the group consisting of N,N-bis(phosphonomethyl)-alanine; N,N-bis(phosphonomethyl)-arginine; N,N-bis(phosphonomethyl)-aspartic acid; N,N-bis(phosphonomethyl)-asparagine; N,N-bis(phosphonomethyl)-cysteine; N,N-bis(phosphonomethyl)-glycine; N,N-bis(phosphonomethyl)-glutamic acid; N,N-bis(phosphonomethyl)-glutamine; N,N-bis(phosphonomethyl)-histidine; N,N-bis(phosphonomethyl)-isoleucine; N,N-bis(phosphonomethyl)-leucine; N,N-bis(phosphonomethyl)-lysine; N,N-bis(phosphonomethyl)-methionine; N,N-bis(phosphonomethyl)-phenylalanine; N,N-bis(phosphonomethyl)-serine; N,N-bis(phosphonomethyl)-threonine; N,N-bis(phosphonomethyl)-tryptophan; N,N-bis(phosphonomethyl)-tyrosine; N,N-bis(phosphonomethyl)-valine; N,N'-bis(phosphonomethyl)-arginine; N,N'-bis(phosphonomethyl)-histidine; N,N'-bis(phosphonomethyl)-lysine and N,N'-bis(phosphonomethyl)-tryptophan.

5. The composition of claim 3, wherein the related compound or compound derived therefrom in a form as a free acid, salt, partial salt, lactone, amide or ester, or in stereoisomeric or non-stereoisomeric form, is selected from the group consisting of N,N-bis(phosphonomethyl)-β-alanine; N,N-bis(phosphonomethyl)-γ-aminobutanoic acid; N,N-bis(phosphonomethyl)-β-aminoisobutanoic acid; N,N-bis(phosphonomethyl)-anserine; N,N-bis(phosphonomethyl)-aminolevulinic acid; N,N-bis(phosphonomethyl)-carnosine; N,N-bis(phosphonomethyl)-canaline; N,N-bis(phosphonomethyl)-canavanine; N,N-bis(phosphonomethyl)-citrulline; N,N-bis(phosphonomethyl)-creatine; N,N-bis(phosphonomethyl)-creatinine; N,N-bis(phosphonomethyl)-cysteine sulfinic acid; N,N-bis(phosphonomethyl)-cystine; N,N-bis(phosphonomethyl)-cycloserine; N,N-bis(phosphonomethyl)-dopa {N,N-bis(phosphonomethyl)-3,4-dihydroxyphenylalanine}; N,N-bis(phosphonomethyl)-dopamine(hydroxytyramine); N,N-bis(phosphonomethyl)-ethionine; N,N-bis(phosphonomethyl)-glutathione; N,N-bis(phosphonomethyl)-guanidinoacetic acid; N,N-bis(phosphonomethyl)-3-guanidinopropanoic acid; N,N-bis(phosphonomethyl)-4-guanidinobutanoic acid; N,N-bis(phosphonomethyl)-homocarnosine; N,N-bis(phosphonomethyl)-homocysteine; N,N-bis(phosphonomethyl)-homoserine; N,N-bis(phosphonomethyl)-4-hydroxyphenylglycine; N,N-bis(phosphonomethyl)-hydroxyglutamic acid; N,N-bis(phosphonomethyl)-hydroxylysine; N,N-bis(phosphonomethyl)-hydroxyproline; N,N-bis(phosphonomethyl)-hypusine; N,N-bis(phosphonomethyl)-homoarginine; N,N-bis(phosphonomethyl)-homocitrulline; N,N-bis(phosphonomethyl)-homocystine; N,Nbis(phosphonomethyl)-homophenylalanine; N,N-bis(phosphonomethyl)-homotryptophan; N,N-bis(phosphonomethyl)-hydroxylysine; N,N-bis(phosphonomethyl)-hydroxyarginine; N,N-bis(phosphonomethyl)-hydroxyhomoarginine; N,N-bis(phosphonomethyl)-hydroxycitrulline; N,N-bis(phosphonomethyl)-hydroxyornithine; N,N-bis(phosphonomethyl)-hydroxyvaline; N,N-bis(phosphonomethyl)-indospicine; N,N-bis(phosphonomethyl)-methoxinine; N,N-bis(phosphonomethyl)-methylarginine; N,N-bis(phosphonomethyl)-methylhistidine; N,N-bis(phosphonomethyl)-methyllysine; N,N-bis(phosphonomethyl)-methylornithine; N,N-bis(phosphonomethyl)-methylserine; N,N-bis(phosphonomethyl)-norvaline; N,N-bis(phosphonomethyl)-ornithine; N,N-bis(phosphonomethyl)-oxalysine; N,N-bis(phosphonomethyl)-penicillamine(N-phosphonomethyl-dimethylcysteine); N,N-bis(phosphonomethyl)-phenylglycine; N,N-bis(phosphonomethyl)-3-phenylserine; N,N-bis(phosphonomethyl)-sarcosine (N-phosphonomethyl-N-methyl-glycine); N,N-bis(phosphonomethyl)-serotonin (N-phosphonomethyl-hydroxytryptamine); N,N-bis(phosphonomethyl)-taurine; N,N-bis(phosphonomethyl)-tryptamine; N,N-bis(phosphonomethyl)-tyramine and N,N'-bis(phosphonomethyl)-ornithine.

6. The composition of claim 1, wherein the phosphonoalkyl of the N-(phosphonoalkyl)-amino acid compound, related compound or compound derived therefrom is selected from the group consisting of phosphonomethyl, phosphonoethyl, phosphonopropyl, phosphonoisopropyl, phosphonobutyl, phosphonoisobutyl, phosphonopentyl, phosphonoisopentyl, phosphonooctyl and phosphonoisooctyl.

7. The composition of claim 1, wherein the compound is an N-(phosphonoalkyl)-amino acid.

8. The composition of claim 1, wherein the compound is an N-(phosphonomethyl)-amino acid.

9. The composition of claim 8, wherein the N-(phosphonomethyl)-amino acid in a form as a free acid, salt, partial salt, lactone, amide or ester, or in a stereoisomeric or non-stereoisomeric form, is selected from the group consisting of N-(phosphonomethyl)-alanine, N-(phosphonomethyl)-arginine, N-(phosphonomethyl)-asparagine, N-(phosphonomethyl)-aspartic acid, N-(phosphonomethyl)-cysteine, N-(phosphonomethyl)-glutamic acid, N-(phosphonomethyl)-glutamine, N-(phosphonomethyl)-glycine, N-(phosphonomethyl)-histidine, N-(phosphonomethyl)-isoleucine, N-(phosphonomethyl)-leucine, N-(phosphonomethyl)-lysine, N-(phosphonomethyl)-methionine, N-(phosphonomethyl)-phenylalanine, N-(phosphonomethyl)-proline, N-(phosphonomethyl)-serine, N-(phosphonomethyl)-threonine, N-(phosphonomethyl)-tryptophan, N-(phosphonomethyl)-tyrosine and N-(phosphonomethyl)-valine.

10. The composition of claim 1, wherein the N-(phosphonoalkyl)-amino acid compound, related compound or compound derived therefrom in a form as a free acid, salt, partial salt, lactone, amide or ester, or in stereoisomeric or non-stereoisomeric form is selected from the group consisting of N-(phosphonomethyl)-alanine, N-(phosphonomethyl)-aminobutanoic acid, N-(phosphonomethyl)-aminoisobutanoic acid, N-(phosphonomethyl)-anserine, N-(phosphonomethyl)-aminolevulinic acid, N-(phosphonomethyl)-carnosine, N-(phosphonomethyl)-canaline, N-(phosphonomethyl)-canavanine, N-(phosphonomethyl)-citrulline, N-(phosphonomethyl)-creatine, N-(phosphonomethyl)-creatinine, N-(phosphonomethyl)-cysteine sulfinic acid, N-(phosphonomethyl)-cystine, N-(phosphonomethyl)-cycloserine, N-(phosphonomethyl)-dopa[N-(phosphonomethyl)-3,4-dihydroxyphenylalanine], N-(phosphonomethyl)-dopamine(hydroxytyramine), N-(phosphonomethyl)-ethionine, N-(phosphonomethyl)-glutathione, N-(phosphonomethyl)-guanidinoacetic acid, N-(phosphonomethyl)-3-guanidinopropanoic acid, N-(phosphonomethyl)-4-guanidinobutanoic acid, N-(phosphonomethyl)-homocarnosine, N-(phosphonomethyl)-homocysteine, N-(phosphonomethyl)-homoserine, N-(phosphonomethyl)-4-hydroxyphenylglycine, N-(phosphonomethyl)-hydroxyglutamic acid, N-(phosphonomethyl)-hydroxylysine, N-(phosphonomethyl)-hydroxyproline, N-(phosphonomethyl)-hypusine, N-(phosphonomethyl)-homoarginine, N-(phosphonomethyl)-homocitrulline, N-(phosphonomethyl)-homocystine, N-(phosphonomethyl)-homophenylalanine, N-(phosphonomethyl)-homotryptophan, N-(phosphonomethyl)-hydroxylysine, N-(phosphonomethyl)-hydroxyarginine, N(phosphonomethyl)-hydroxyhomoarginine, N-(phosphonomethyl)-hydroxycitrulline, N-(phosphonomethyl)-hydroxyornithine, N-(phosphonomethyl)-hydroxyvaline, N-(phosphonomethyl)-indospicine, N-(phosphonomethyl)-methoxinine, N-(phosphonomethyl)-methylarginine, N-(phosphonomethyl)-methylhistidine, N-(phosphonomethyl)-methyllysine, N-(phosphonomethyl)-methylornithine, N-(phosphonomethyl)-methylserine, N-(phosphonomethyl)-norvaline, N-(phosphonomethyl)-ornithine, N-(phosphonomethyl)-oxalysine, N-(phosphonomethyl)-penicillamine(N-phosphonomethyl-dimethylcysteine), N-(phosphonomethyl)-phenylglycine, N-(phosphonomethyl)-3-phenylserine, N-(phosphonomethyl)-sarcosine (N-phosphonomethyl-N-methyl-glycine), N-(phosphonomethyl)-serotonin (N-phosphonomethyl-hydroxytryptamine), N-(phosphonomethyl)-taurine, N-(phosphonomethyl)-tryptamine and N-(phosphonomethyl)-tyramine.

11. The composition of claim 1, wherein the N-(phosphonoalkyl)-amino acid compound, related compound or compound derived therefrom in a form as a free acid, salt, partial salt, lactone, amide or ester, or in stereoisomeric or non-stereoisomeric form, is selected from the group consisting of N-(phosphonomethyl)-asparagine, N-(phosphonomethyl)-asparaginamide, N-(phosphonomethyl)-aminobutanoic acid, N-(phosphonomethyl)-arginine, N-(phosphonomethyl)-argininamide, N-(phosphonomethyl)-arginine ethyl ester, N-(phosphonomethyl)-creatine, N-(phosphonomethyl)-creatinine, N-(phosphonomethyl)-cysteine, N-(phosphonomethyl)-glutamic acid, N-(phosphonomethyl)-glutamic acid diethyl ester, N-(phosphonomethyl)-glutamine, N-(phosphonomethyl)-glutaminamide, N-(phosphonomethyl)-glutamine ethyl ester, N-(phosphonomethyl)-glutathione, N-(phosphonomethyl)-glycine, N-(phosphonomethyl)-glycinamide, N-(phosphonomethyl)-glycine ethyl ester, N-(phosphonomethyl)-glycine propyl ester, N-(phosphonomethyl)-glycine isopropyl ester, N-(phosphonomethyl)-4-hydroxyphenylglycine, N-(phosphonomethyl)-lysine, N-(phosphonomethyl)-lysinamide, N-(phosphonomethyl)-lysine ethyl ester, N-(phosphonomethyl)-ornithine, N-(phosphonomethyl)-proline, N-(phosphonomethyl)-prolinamide, N-(phosphonomethyl)-proline ethyl ester, N-(phosphonomethyl)-proline propyl ester, N-(phosphonomethyl)-proline isopropyl ester, N-(phosphonomethyl)-serine, N-(phosphonomethyl)-tyrosine and N-(phosphonomethyl)-tyramine.

12. The composition of claim 1, wherein the composition further comprises a cosmetic or pharmaceutical agent.

13. The composition of claim 12, wherein the cosmetic or pharmaceutical agent is selected from the group consisting of hydroxyacids, ketoacids and related compounds; phenyl alpha acyloxyalkanoic acids and derivatives; N-acyl-aldosamines, N-acylamino acids and related N-acyl compounds; local analgesics and anesthetics; anti-acne agents; anti-bacterial agents; anti-yeast agents; anti-fungal agents; anti-viral agents; anti-infective agents; anti-dandruff agents; anti-dermatitis agents; anti-eczema agents; anti-histamine agents; anti-pruritic agents; anti-emetics; anti-motion sickness agents; anti-inflammatory agents; anti-hyperkeratotic agents; antiperspirants; anti-psoriatic agents; anti-rosacea agents; anti-seborrheic agents; hair conditioners and hair treatment agents; anti-aging and anti-wrinkle agents; anti-anxiety agents; anti-convulsant agents; anti-depressant agents; sunblock and sunscreen agents; skin lightening agents; depigmenting agents; astringents; cleansing agents; corn, callus or wart removing agents; skin plumping agents; skin volumizing agents; skin firming agents; matrix metalloproteinase (MMP) inhibitors; topical cardiovascular agents; wound-healing agents; gum disease or oral care agents; amino acids; peptides; dipeptides; tripeptides; glutathione and its derivatives; oligopeptides; polypeptides; carbohydrates; aminocarbohydrates; vitamins; corticosteroids; tanning agents; hormones and retinoids.

14. The composition of claim 12, wherein the cosmetic or pharmaceutical agent as stated or as free base, free acid, ester, amide, lactone or salt form is selected from the group consisting of: abacavir, abciximab, acamprosate, acarbose, acebutolol, acetaminophen, acetaminosalol, acetazolamide, acetic acid, acetohydroxamic acid, N-acetylcysteine and its esters, N-acetylglutathione and its esters, acitretin, aclometasone dipropionate, acrivastine, acthrel, actidose, actigall, acyclovir, adalimumab, adapalene, adefovir dipivoxil, adenosine, agalsidase, albendazole, albumin, albuterol, aldesleukin, alefacept, alemtuzumab, alendronate, alfuzosin, alitretinoin, allantoin, allium, allopurinol, alloxanthine, almotriptan, alosetron, alpha tocipheral, alpha$_1$-proteinase, alprazolam, alprenolol, alprostadil, alteplase, altretamine, aluminum acetate, aluminum chloride, aluminum chlorohydroxide, aluminum hydroxide, amantadine, amifostine, amiloride, aminacrine, amino acid, aminobenzoate, p-aminobenzoic acid, aminocaproic acid, aminohippurate, aminolevulinic acid, aminosalicylic acid, amiodarone, amitriptyline, amlodipine, amocarzine, amodiaquin, amorolfine, amoxapine, amoxicillin, amphetamine, amphotericin, ampicillin, amprenavir, anagrelide, anakinra, anastrozole, anisindione, anthralin, antihemophilic, antithrombin, anti-thymocyte, antivenin, apomorphine, aprepitant, aprotinin, arbutin, argatroban, aripiprazole, arnica, ascorbic acid and its esters, ascorbyl palmitate, aspirin, atazanavir, atenolol, atomoxetine, atorvastatin, atovaquone, atropine, azathioprine, azelaic acid, azelastine, azithromycin, baclofen, bacitracin, balsalazide, balsam, basiliximab, beclomethasone dipropionate, bemegride, benazepril, bendroflumethiazide, benzocaine, benzonatate, benzophenone, benzoyl peroxide, benztropine, bepridil, beta carotene, betamethasone dipropionate, betamethasone valerate, betaxolol, bethanechol, bevacizumab, bexarotene, bicalutamide, bimatoprost, bioflavonoids, biotin, biperiden, bisacodyl, bisoprolol, bivalirudin, bortezomib, bosentan, botulinum, brimonidine, brinzolamide, bromocriptine, brompheniramine, budesonide, bumetanide, bupivacaine, buprenorphine, bupropion, burimamide, buspirone, busulfan, butabarbital, butalbital, butenafine, butoconazole, butorphanol, butyl aminobenzoate, cabergoline, caffeic acid, caffeine, calcipotriene, calcitonin-salmon, calcitriol, calfactant, camellia sinensis, camphor, candesartan cilexetil, capecitabine, capreomycin, capsaicin, captopril, carbamazepine, carbamide peroxide, carbidopa, carbinoxamine, cefditoren pivoxil, cefepime, cefpodoxime proxetil, celecoxib, cetirizine, cevimeline, chitosan, chlordiazepoxide, chlorhexidine, chloroquine, chlorothiazide, chloroxylenol, chlorpheniramine, chlorpromazine, chlorpropamide, ciclopirox, cilostazol, cimetidine, cinacalcet, ciprofloxacin, citalopram, citric acid, cladribine, clarithromycin, clemastine, clindamycin, clioquinol, clobetasol propionate, clocortolone pivalate, clomiphene, clonidine, clopidogrel, clotrimazole, clozapine, coal tar, coal tar extracts (LCD), codeine, cromolyn, crotamiton, cyclizine, cyclobenzaprine, cycloserine, cytarabine, dacarbazine, dalfopristin, dapsone, daptomycin, daunorubicin, deferoxamine, dehydroepiandrosterone, delavirdine, desipramine, desloratadine, desmopressin, desoximetasone, dexamethasone, dexmedetomidine, dexmethylphenidate, dexrazoxane, dextroamphetamine, diazepam, diclofenac, dicyclomine, didanosine, dihydrocodeine, dihydromorphine, diltiazem, 6,8-dimercaptooctanoic acid (dihydrolipoic acid), diphenhydramine, diphenoxylate, dipyridamole, disopyramide, dobutamine, dofetilide, dolasetron, donepezil, dopa esters, dopamide, dopamine, dorzolamide, doxepin, doxorubicin, doxycycline, doxylamine, doxepin, duloxetine, dyclonine, econazole, efalizumab, eflomithine, eletriptan, emtricitabine, enalapril, ephedrine, epinephrine, epinine, epirubicin, eptifibatide, ergotamine, erythromycin, escitalopram, esmolol, esomeprazole, estazolam, estradiol, etanercept, ethacrynic acid, ethinyl estradiol, etidocaine, etomidate, famciclovir, famotidine, felodipine, fentanyl, ferulic acid, fexofenadine, flecamide, fluconazole, flucytosine, fluocinolone acetonide, fluocinonide, 5-fluorouracil, fluoxetine, fluphenazine, flurazepam, fluticasone propionate, fluvoxamine, formoterol, furosemide, galactarolactone, galactonic acid, galactonolactone, galantamine, gatifloxacin, gefitinib, gemcitabine, gemifloxacin, glucarolactone, gluconic acid, gluconolactone, glucuronic acid, glucuronolactone, glycolic acid, griseofulvin, guaifenesin, guanethidine, N-guanylhistamine, haloperidol, haloprogin, hexylresorcinol, homatropine, homosalate, hydralazine, hydrochlorothiazide, hydrocortisone, hydrocortisone 21-acetate, hydrocortisone 17-butyrate, hydrocortisone 17-valerate, hydrogen peroxide, hydromorphone, hydroquinone, hydroquinone monoether, hydroxyzine, hyoscyamine, hypoxanthine, ibuprofen, ichthammol, idarubicin, imatinib, imipramine, imiquimod, indinavir, indomethacin, infliximab, irbesartan, irinotecan, isoetharine, isoproterenol, itraconazole, kanamycin, ketamine, ketanserin, ketoconazole, ketoprofen, ketotifen, kojic acid, labetalol, lactic acid, lactobionic acid, lamivudine, lamotrigine, lansoprazole, letrozole, leuprolide, levalbuterol, levofloxacin, lidocaine, linezolid, lobeline, loratadine, loperamide, losartan, loxapine, lysergic diethylamide, mafenide, malic acid, maltobionic acid, mandelic acid, maprotiline, mebendazole, mecamylamine, meclizine, meclocycline, memantine, menthol, meperidine, mepivacaine, mequinol, mercaptopurine, mescaline, metanephrine, metaproterenol, metaraminol, metformin, methadone, methamphetamine, methotrexate, methoxamine, methyldopa esters, methyldopamide, 3,4-methylenedioxymethamphetamine, methyllactic acid, methyl nicotinate, methylphenidate, methyl salicylate, metiamide, metolazone, metoprolol, metronidazole, mexiletine, miconazole, midazolam, midodrine, miglustat, minocycline, minoxidil, mirtazapine, mitoxantrone, moexiprilat, molindone, monobenzone, morphine, moxifloxacin, moxonidine, mupirocin, nadolol, naftifine, nalbuphine, nalmefene, naloxone, naproxen, nefazodone, nelfinavir, neomycin, nevirapine, nicardipine, nicotine, nifedipine, nimodipine, nisoldipine, nitrofurantoin, nizatidine, norepinephrine, nystatin, octopamine, octreotide, octyl methoxycinnamate, octyl salicylate, ofloxacin, olanzapine, olmesartan medoxomil, olopatadine, omeprazole, ondansetron, oxiconazole, oxotremorine, oxybenzone, oxybutynin, oxycodone, oxymetazoline, padimate O, palonosetron, pantothenic acid, pantoyl lactone, paroxetine, pemoline, penciclovir, penicillamine, penicillins, pentazocine, pentobarbital, pentostatin, pentoxifylline, pergolide, perindopril, permethrin, phencyclidine, phenelzine, pheniramine, phenmetrazine, phenobarbital, phenol, phenoxybenzamine, phentolamine, phenylephrine, phenylpropanolamine, phenyloin, physostigmine, pilocarpine, pimecrolimus, pimozide, pindolol, pioglitazone, pipamazine, piperonyl butoxide, pirenzepine, podofilox, povidone iodine, pramipexole, pramoxine, prazosin, prednisone, prenalterol, prilocalne, procainamide, procaine, procarbazine, promazine, promethazine, promethazine propionate, propafenone, propoxyphene, propranolol, propylthiouracil, protriptyline, pseudoephedrine, pyrethrin, pyrilamine, pyrimethamine, quetiapine, quinapril, quinethazone, quinidine, quinupristin, rabeprazole, reserpine, resorcinol, retinal, 13-cis retinoic acid, retinoic acid, retinol, retinyl acetate, retinyl palmitate, ribavirin, ribonic acid, ribonolactone, rifampin, rifapentine, rifaximin, riluzole, rimantadine, risedronic acid, risperidone, ritodrine, rivastigmine, rizatriptan, ropinirole, ropivacaine, salicylamide, salicylic acid, salmeterol, scopolamine, selegiline, selenium sulfide, serotonin, sertaconazole, sertindole, sertraline, shale tar, sibutramine, sildenafil, sotalol, streptomycin, strychnine, sulconazole, sulfacetamide, sulfabenz, sulfabenzamide, sulfabromomethazine, sulfacetamide (sodium sulfacetamide), sulfachlorpyridazine, sulfacytine, sulfadiazine, sulfadimethoxine, sulfadoxine, sulfaguanole, sulfalene, sulfamethizole, sulfamethoxazole, sulfanilamide, sulfapyrazine, sulfapyridine, sulfasalazine, sulfasomizole, sulfathiazole, sulfisoxazole, sulfur, tacrolimus, tadalafil, tamsulosin, tartaric acid, tazarotene, tegaserod, telithromycin, telmisartan, temozolomide, tenofovir disoproxil, terazosin, terbinafine, terbutaline, terconazole, terfenadine, tetracaine, tetracycline, tetrahydrozoline, thalidomide, theobromine, theophylline, thiabendazole, thioctic acid (lipoic acid), thioridazine, thiothixene, thymol, tiagabine, timolol, timidazole, tioconazole, tirofiban, tizanidine, tobramycin, tocamide, tolazoline, tolbutamide, tolnaftate, tolterodine, tramadol, tranylcypromine, trazodone, triameinolone acetonide, triamcinolone diacetate, triamcinolone hexacetonide, triamterene, triazolam, triclosan, triflupromazine, trimethoprim, trimipramine, tripelennamine, triprolidine, tromethamine, tropic acid, tyramine, undecylenic acid, urea, urocanic acid, ursodiol, valacyclovir, vardenafil, venlafaxine, verapamil, vitamin E acetate, voriconazole, warfarin, wood tar, xanthine, zafirlukast, zaleplon, zinc pyrithione, ziprasidone, zolmitriptan and zolpidem.

15. The composition of claim 1,
wherein the treatment of a cosmetic condition or dermatological disorder is treatment of a cosmetic condition of dermatological disorder selected from the group consisting of disturbed keratinization; changes associated with intrinsic and extrinsic aging; acne; rosacea; age spots; blemished skin; blotches; cellulite; dermatoses; dermatitis; skin, nail and hair infections; dandruff; dryness or looseness of skin, nail and hair; xerosis; eczema; elastosis; herpes; hyperkeratosis; hyperpigmented skin; ichtyosis; keratoses; lentigines; melasmas; mottled skin; pseudofolliculitis barbae; photoaging and photodamage; pruritus; psoriasis; skin lines; stretch marks; thinning of skin, nail plate and hair; warts; wrinkles; breakdown, defective synthesis or repair of dermal components; abnormal or diminished synthesis of collagen, glycosaminoglycans, proteoglycans or elastin, diminished levels of collagen, glycosaminoglycans, proteoglycans or elastin in the dermis; uneven skin tone; uneven and rough surface of skin, nail and hair; loss or reduction of skin, nail and hair resiliency, elasticity and recoilability; laxity; lack of skin, nail and hair lubricants and luster; fragility and splitting of nail and hair, yellowing skin; reactive, irritating or telangiectatic skin; dull and older-looking skin, nail and hair; or
wherein the treatment of a cosmetic condition or dermatological disorder is for general care of skin, nail and hair; to improve skin texture and pores, flakiness and redness; to make skin soft, smooth, fresh, balanced, visibly clear, even-toned and brighter; to increase skin fullness and plumpness; for skin bleach and lightning; or wound healing.

16. The composition of claim 1, wherein the N-(phosphonoalkyl)-amino acid is N-(phosphonomethyl)-glycine and the composition is used for systemic administration to the mammalian subject for treatment of a cosmetic condition or dermatological disorder.

17. The composition of claim 16, wherein the cosmetic condition or dermatological disorder is selected from the group consisting of disturbed keratinization; acne; hyperkeratosis and ichthyosis.

* * * * *